United States Patent [19]
Kurtz et al.

[11] Patent Number: 5,824,694
[45] Date of Patent: Oct. 20, 1998

[54] THIAZOLIDINE DERIVATIVES FOR THE TREATMENT OF PSORIASIS

[75] Inventors: Theodore W. Kurtz, Mill Valley; Harrihar A. Pershadsingh, Bakersfield, both of Calif.

[73] Assignee: Bethesda Pharmaceuticals, Inc., Mill Valley, Calif.

[21] Appl. No.: 639,942

[22] Filed: Apr. 18, 1996

Related U.S. Application Data

[63] Continuation of Ser. No. 460,384, Jun. 2, 1995, abandoned, and a continuation of Ser. No. 263,446, Jun. 22, 1994, Pat. No. 5,594,015.

[51] Int. Cl.$^6$ ............................................. A61K 31/425
[52] U.S. Cl. .................. 514/369; 514/299; 514/342; 514/367; 514/370
[58] Field of Search .................... 514/369, 370, 514/367, 299; 174/342

[56] References Cited

U.S. PATENT DOCUMENTS

| | | | |
|---|---|---|---|
| 4,444,779 | 4/1984 | Kawamatsu | 424/263 |
| 4,461,902 | 7/1984 | Kawamatsu | 548/183 |
| 4,486,594 | 12/1984 | Kawamatsu | 548/183 |
| 4,572,912 | 2/1986 | Yoshioka | 514/369 |
| 4,582,839 | 4/1986 | Meguro | 514/342 |
| 4,703,052 | 10/1987 | Eggler | 514/337 |
| 4,725,610 | 2/1988 | Meguro | 514/369 |
| 4,775,687 | 10/1988 | Meguro | 514/369 |
| 4,812,570 | 3/1989 | Meguro | 546/280 |
| 5,002,953 | 3/1991 | Hindley | 514/275 |
| 5,023,085 | 6/1991 | Francoeur et al. | 424/449 |
| 5,053,420 | 10/1991 | Pershadsingh | 514/369 |
| 5,143,928 | 9/1992 | Cetenko | 514/364 |
| 5,252,735 | 10/1993 | Morris | 544/121 |

FOREIGN PATENT DOCUMENTS

| | | |
|---|---|---|
| 0277836 | 8/1988 | European Pat. Off. . |
| 56071081 | 10/1979 | Japan . |
| 201775183 | 11/1983 | Japan . |
| WO 91/12003 | 8/1981 | WIPO . |

OTHER PUBLICATIONS

Barry, Brian W., Dermatological Formulations, 1983: pp. 181–186.

Colca et al., Ciglitazone, A Hypoglycemic Agent: Early Effects on the Pancreatic Islets of Ob/Ob Mice, *Metabolism*, vol. 37, No. 3 (Mar.), 1988: pp. 276–280.

Chang et al., Ciglitazone, a New Hypoglycemic Agent, *Diabetes*, vol. 32 (Sep.), 1983: pp. 830–838.

Wyrick et al., Effects of Molecular Modification on Hypocholesteremic Activity of 1,3–Bis (substituted phenoxy)—2–propanones and Related Derivatives, *Journal of Medicinal Chemistry*, vol. 21, 1978: pp. 386–390.

Zask et al., Synthesis and Antihyperglycemic Activity of Novel 5–(Naphthalenylsulfony)–2, 4–thiazolidinediones, *J. Med. Chem*, vol. 33, 1990: pp. 1418–1423.

Boyce et al., Calcium–Regulated Differentiation of Normal Human Epidermal Keratinocytes in Chemically Defined Clonal Culture and Serum–Free Serial Culture, *The Journal of Investigative Dermatology*, vol. 81, 1983: pp. 33s–40s.

Kitano et al., Suppression of Proliferation of Human Epidermal Keratinocytes by 1, 25–dihydroxyvitamin $D_3$, *European Journal of Clinical Investigation*, vol. 21, 1991: pp. 53–58.

West et al., Simple Assays of Retiniod Activity As Potential Screens For Compounds That May Be Useful In Treatment Of Psoriasis, *The Society for Investigative Dermatology, Inc.*, vol. 100, 1992: pp. 95–100.

Menter et al., Psoriasis in Practice, *The Lancet*, vol. 338, (Jul. 27) 1991: pp. 231–234.

Barker, The Pathophysiology of Psoriasis, *The Lancet*, vol. 338, (Jul. 27) 1991: pp. 227–230.

*Primary Examiner*—Paul J. Killos
*Attorney, Agent, or Firm*—Townsend and Townsend and Crew LLP

[57] ABSTRACT

A new medical use for certain thiazolidine derivatives is disclosed. Specifically, treatment of hyperproliferative epithelial cell conditions, such as psoriasis, by administration of thiazolidinediones or 5'-aryl substituted thiazolidine derivatives is described. Appropriate chemical structures, synthetic reactions, formulations, routes of administration and dosages are included.

21 Claims, 8 Drawing Sheets

THIAZOLIDINE DERIVATIVES FOR THE TREATMENT OF PSORIASIS

This is a Continuation of application No. 08/460,384, filed Jun. 2, 1995, (now abandoned), and is a Rule 60 Continuation of application No. 08/263,446, filed Jun. 22, 1994, U.S. Pat. No. 5,594,015.

BACKGROUND OF THE INVENTION

1. Field of the Invention

This invention relates to an additional medical use of thiazolidinediones, some of which are used in the treatment of diabetes and essential hypertension. These compounds are also useful for the treatment of psoriasis and other diseases including acne.

2. Background

Psoriasis is a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Arthritis is sometimes associated with psoriasis, and it may be crippling. Psoriasis afflicts about 1–2% of the United States population with about 200,000 new cases diagnosed annually. Some estimate that there are up to five million patients with psoriasis in the United States.

Hyperproliferation of keratinocytes is a key feature of psoriasis along with epidermal inflammation and reduced differentiation of keratinocytes. Multiple mechanisms have been invoked to explain the keratinocyte hyperproliferation that characterizes psoriasis. However, no single mechanism has been definitively implicated. Activation of epidermal growth factor receptors, alterations in protein kinase C signal transduction pathways, and the attendant changes in intracellular calcium metabolism may play a role in psoriatic epidermal hyperplasia. Disordered cellular immunity has also been implicated in the pathogenesis of psoriasis. However, the exact mechanisms of keratinocyte hyperproliferation and epidermal inflammation remain unclear.

Because of the multifactorial nature of psoriasis, it is difficult to predict whether pharmacologic manipulation of complex signal transduction pathways, growth factor receptors, or cellular immune functions will attenuate the hyperproliferation of keratinocytes. A number of diverse pharmacologic therapies have been tried with varying degrees of success. Current treatments of psoriasis include tar based therapies, psoralens with ultraviolet light, immunosuppressants such as cyclosporine and methotrexate, glucocorticoids, retinoids, and vitamin D analogs.

Although the current therapies for psoriasis share the common feature of inhibiting hyperproliferation of keratinocytes, they act through different cellular mechanisms and are accompanied by a variety of side effects that are at best unpleasant and often dangerous. For instance, tar based therapies are uncomfortable and a nuisance to apply. Immunosuppressants like methotrexate can predispose to malignancy, cyclosporine can cause renal damage and hypertension, glucocorticoids can cause local and serious systemic side effects such as adrenal suppression, vitamin D analogs can cause disordered calcium metabolism, and retinoids can have a broad range of side effects and are teratogens. Because of the distressing and disfiguring nature of psoriasis and the unsatisfactory aspects of current therapies, there is considerable interest in developing alternative therapeutic approaches to treating this hyperproliferative skin disorder.

SUMMARY OF THE INVENTION

The invention provides methods for the treatment of psoriasis by effective dosages of thiazolidine derivatives known as thiazolidinediones. These compounds can also be used according to the invention to treat other disorders involving epidermal or epithelial cell proliferation. Examples of these disorders include eczema; lupus associated skin lesions; psoriatic arthritis; rheumatoid arthritis that involves hyperproliferation and inflammation of epithelial-related cells lining the joint capsule; dermatitides such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis.

The thiazolidinediones have the advantage over conventional therapy of targeting the problem of psoriatic epidermal hyperplasia without disrupting the immune system, predisposing to cancer, or causing renal damage and hypertension. Additionally, they are convenient to administer.

In human keratinocytes proliferating in culture, according to the invention, the thiazolidinedione ciglitazone caused a dose-dependent inhibition of keratinocyte cell growth. Based on the discovery that thiazolidinediones have a potent ability to attenuate proliferation of human keratinocytes, the invention includes the novel approach of using these agents to treat psoriasis, a disorder of keratinocyte hyperproliferation.

DETAILED DESCRIPTION

Figure 1:
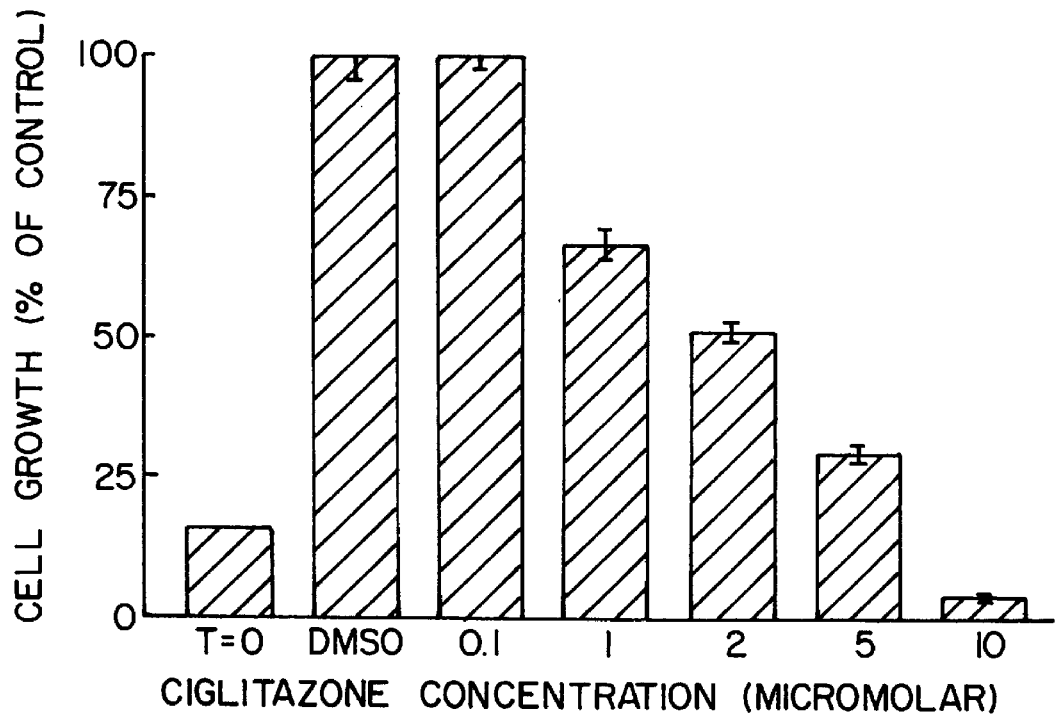
FIG. 1 shows a dose response graph of the application of ciglitazone to skin cells (keratinocytes) taken from an adult human, subject A, and grown in cell culture.

The invention provides therapeutic compositions and methods for treating psoriasis. The active ingredients of the compositions are well-known compounds which are generally described as 5'-aryl substituted thiazolidine derivatives or thiazolidinediones. These compounds are conventionally known for the treatment of diabetes. Particular examples are ciglitazone, pioglitazone (also known as AD-4833 and U-72107E), englitazone (also known as CP-68,722), and troglitazone (also know as CS-045 (Sankyo) and CI-991 (Park-Davis)).

Some of the therapeutic compounds of this invention are known as anti-diabetic agents which lower the concentration of glucose and lipids in the blood. Representative compounds comprise those of U.S. Pat. Nos. 4,812,570, 4,775,687, 4,725,610, 4,582,839, 4,572,912, 4,486,594, 4,461,902, 4,444,779 and European Pat. No. 0277,836. Other thiazolidine compounds have been described as anti-hypertensive agents. See U.S. Pat. No. 5,053,420 and Japanese Pat. No. 56071081.

A thiazolidine compound used to demonstrate the antipsoriatic activity of thiazolidine compounds was ciglitazone, which is also a known anti-diabetic agent. Colca, J. R. et al., Ciglitazone, A Hypoglycemic Agent: Early Effects on the Pancreatic Islets of Ob/Ob Mice, *Metabolism,* 37: 276–280 (1988); and Chang, A. Y. et al., Ciglitazone, A New Hypoglycemic Agent, *Diabetes* 32: 830–838 (1983).

1. Structures of Therapeutic Compounds

Thiazolidinediones conform to the following structural formula I:

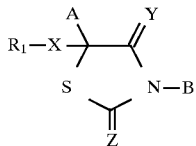

where variable ring substituents are defined below.
A is H or methyl;
B is H or methyl;
X is a lower alkylene or a bond; or —HC=CH—; or O, $CH_2$, $CH_2S$, $CH_2SO_2$, S, SO, or $SO_2$;
Y is oxo or imino;
Z is oxo or imino; and
$R_1$ is a structurally diverse variable comprised of the several compositions detailed as follows.

$R_1$ may be an aromatic carbocyclic or aromatic heterocyclic or substituted benzyl with X as a lower alkylene. More particularly, $R_1$ may be of the formula IIa

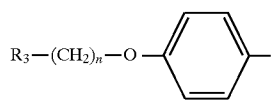

where n is an integer from 1 to 4, and where $R_3$ is of the formula IIb

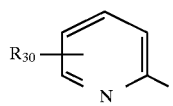

where $R_{30}$ is a lower alkyl of 1–4 carbons; or $R_3$ is of the formula IIc

where $R_{31}$ is hydrogen or a lower alkyl of 1–4 carbons and the cyclohexane ring may be optionally substituted at any available methylene with single oxo or hydroxy; or $R_3$ is of the formula IId

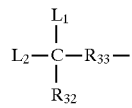

wherein $R_{32}$ is alkyl, cycloalkyl, phenylalkyl, phenyl, a five- or six-membered heterocyclic group including one or two hetero-atoms selected from the group consisting of nitrogen, oxygen and sulfur, or a group of the formula IIe

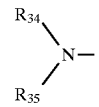

where
$R_{34}$ and $R_{35}$ are the same or different and each is lower alkyl or $R_{34}$ and $R_{35}$ are combined to each other either directly or as interrupted by a hetero-atom selected from the group consisting of nitrogen, oxygen and sulfur to form a five- or six-membered ring as taken together with the nitrogen atom adjacent to $R_{34}$ and $R_{35}$;
$R_{33}$ is a bond or a lower alkylene group, $L_1$ and $L_2$ may be the same or different and each is a lower alkyl or $L_1$ and $L_2$ are combined to each other to form an alkylene group, provided that when $R_{32}$ is other than alkyl, $L_1$ and $L_2$ may further be hydrogen; or
$R_3$ is of the formula IIf

wherein A' is a substituted or unsubstituted aromatic heterocycly group and A" is an H, an alkyl group, an acyl group, an aralkyl group, wherein the aryl moiety may be substituted or unsubstituted, or a substituted or unsubstituted aryl group.

Examples of compounds comprising thiazolidines derivatized with groups Ia, IIb, IIc, IId and IIe are:

5-{4-[2-(5-ethyl-2-pyridyl)ethoxy]benzyl}-2,4-thiazolidinedione (commonly called pioglitazone);

5-[4-(1-methylcyclohexylmethoxybenzyl]thiazolidine dione (commonly called ciglitazone);

5-[4-(o-3-hydroxy-1-methyl-r-1-cyclohexylmethoxy) benzyl]-thiazolidine-2,4-dione;

5-{4-[2-(4-methyl-5-thiazolyl)ethoxy] benzyl}thiazolidine-2,4-dione;

5-{4-[2-(4-methyl-5-pyridyl)ethoxylbenzyl]thiazo]idine-2,4-dione; and 5-(4-[2-(N-methyl-N-(2-benzothiazolyl)amino)ethoxy]
benzoyl-2,4-thiazolidinedione.

The thiazolidine derivative may further be selected from compounds where X is methylene and $R_1$ is of the formula IV

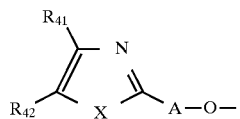

wherein X is an oxygen or sulfur atom, $R_{41}$ and $R_{42}$ are each independently hydrogen or a hydrocarbon residue which may optionally be substituted and $R_{41}$ and $R_{42}$ may jointly, together with the oxazole or thiazole ring, form a condensed ring and A is a lower alkylene group. Examples include:

5-{4-[2-(5-methyl-4-phenyl-2-oxazoyl)ethoxy]benzyl}-2,4-thiazolidinedione; and,

5-[4-(4-phenyl-2-thiazolylmethoxy)benzyl]-2,4-thiazolidinedione.

The thiazolidine may further be selected from compounds where X is methylene or —HC=CH— and $R_1$ is of formula V

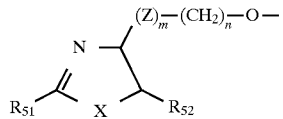

wherein $R_{51}$ is hydrogen or a hydrocarbon residue or heterocyclic residue which may each be substituted;

$R_{52}$ is hydrogen or a lower alkyl group which may be substituted by hydroxyl group;

X is an oxygen or sulfur atom;

Z is a hydroxylated methylene or carbonyl;

m is 0 or 1;

n is an integer of 1 to 3; and pharmaceutically acceptable salts. Examples include:

5-[4-(2-phenyl-4-oxazolylmethoxy)benzyl]-2,4-thiazolidinedione;

5-[4-(5-methyl-2-phenyl-4-oxazolylmethoxy)benzyl]-2,4-thiazolidinedione; and,

5-{4-[2-(5-bromomethyl-2-phenyl-4-oxazolyl)ethoxy]benzyl}-2,4-thiazolidinedione.

The thiazolidine derivative may be further selected from compounds where X is methylene and $R_1$ is of formula VI

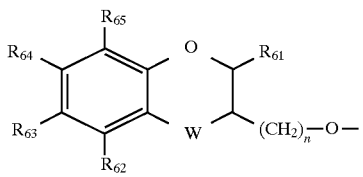

wherein $R_{61}$ and $R_{62}$ are the same or different and each represents a hydrogen atom or a $(C_1-C_5)$ alkyl group;

$R_{63}$ represents a hydrogen atom, a $(C_1-C_6)$ aliphatic acyl group, an alicyclic acyl group, an aromatic acyl group, a heterocyclic acyl group, an araliphatic acyl group, a $(C_1-C_6$ alkoxy) carbonyl group or an aralkyloxycarbonyl group;

$R_{64}$ and $R_{65}$ are the same or different and each represents a hydrogen atom, a $(C_1-C_5)$ alkyl group or a $(C_1-C_5)$ alkoxy group, or $R_{64}$ and $R_{65}$ together represent a $(C_1-C_4)$ alkylenedioxy group;

W represents the —CH2—, >CO or >CH—O-$R_{66}$ group (in which $R_{66}$ represents any one of the atoms or groups defined for $R_{63}$ and may be the same as or different from $R_{63}$, and where n is an integer from 1 to 10. Examples of such compounds include:

5-[4-(6-fluoro-2-methylchroman-2-yl methoxy)benzyl] thiazolidine-2,4-dione;

5-[4-6-fluoro-2-methyl-4-oxochroman-2yl methoxy) benzyl]thiazolidine-2,4-dione;

5-[4-(6-acetyl-7-hydroxy-2,8-dimethyl-4-oxochroman-2-yl methoxy)benzyl]thiazolidine-2,4-dione; and 5-[4-(2,5,7-trimethylchroman-2-yl methoxy)benzyl] thiazolidine-2,4-dione.

The thiazolidine derivative may be further selected from compounds where X is methylene and $R_1$ is of formula VII

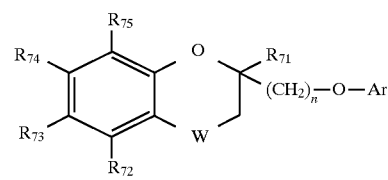

wherein:

$R_{71}$ represents a hydrogen atom, a $(C_1-C_{25})$ alkyl group, a $(C_3-C_{10})$ cycloalkyl group or a substituted $(C_3-C_{10})$ cycloalkyl group having at least one $(C_1-C_6)$ alkyl substituent;

$R_{72}$, $R_{74}$ and $R_{75}$ are the same or different and each represents: a hydrogen atom; a $(C_1-C_{25})$ alkyl group; a substituted $(C_1-C_{26})$ having at least one of substituents (a); an aralkyl group; a $(C_3-C_{10})$ cycloalkyl group; a substituted $(C_3-C_{10})$ cycloalkyl group having at least one $(C_1-C_6)$ alkyl substituent; and aryl group; a halogen atom; a hydroxy group; a protected hydroxy group in which the protecting group is selected from substituents (b); a $(C_1-C_7)$ alkanoyl group; a substituted $(C_2-C_7)$ alkanoyl group having at least one of substituents (c); an arylcarbonyl group; a cycloalkylcarbonyl group in which the cycloalkyl part is $(C_3-C_{10})$; a substituted cycloalkylcarbonyl group in which the cycloalkyl part is $(C_3-C_{10})$ and has at least one $(C_1-C_6)$ alkyl substituent; a carboxy group; a $(C_2-C_7)$ alkoxycarbonyl group; an aryloxycarbonyl group; and aralkyloxycarbonyl group; a nitro group; a group of formula VIIb

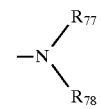

in which $R_{77}$ and $R_{78}$ are the same or different and each represents a hydrogen atom, a $(C_1-C_6)$ alkyl group, an aralkyl group, a $(C_3-C_{10})$ cycloalkyl group, an aryl group, a $(C_1-C_7)$ alkanoyl group, an aralkanoyl group, an arylcarbonyl group or a $(C_2-C_7)$ alkoxycarbonyl group, or $R_{77}$ and $R_{78}$, together with the nitrogen atom to which they are attached, form a nitrogen-containing heterocyclic group having from 5 to 10 ring atoms, of which one is said nitrogen atom and from 0 to 3 are additional nitrogen and/or oxygen and/or sulphur hetero-atoms;

or a group of formula VIIc

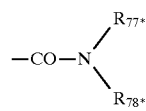

in which
- $R_{77*}$ and $R_{78*}$ are the same or different and each represents a hydrogen atom, a ($C_1$–$C_6$) alkyl group, an aralkyl group, a ($C_3$–$C_{10}$) cycloalkyl group or an aryl group or $R_{77}$ and $R_{78}$, together with the nitrogen atom to which they are attached, form a nitrogen-containing heterocyclic group having from 5 to 10 ring atoms, of which one is said nitrogen atom and from 0 to 3 are independently additional nitrogen or oxygen or sulphur hetero-atoms;
- $R_{73}$ represents a hydrogen atom, a ($C_1$–$C_{25}$) alkyl group, a substituted ($C_1$–$C_{25}$) alkyl group having at least one of substituents (a), an aralkyl group, a ($C_3$–$C_{10}$) cycloalkyl group, a substituted ($C_3$–$C_{10}$) cycloalkyl group having at least one ($C_1$–$C_6$) alkyl substituent, an aryl group, a halogen atom, a ($C_1$–$C_7$) alkanoyl group, a substituted ($C_2$–$C_7$) alkanoyl group having at least one of substituents (c), an arylcarbonyl group, a cycloalkylcarbonyl group in which the cycloalkyl pat is ($C_3$–$C_{10}$), a substituted cycloalkylcarbonyl group in which the cycloalkyl part is ($C_3$–$C_{10}$) and has at least one ($C_1$–$C_6$) alkyl substituent, a carboxy group, a ($C_2$–$C_7$) alkoxycarbonyl group, an aryloxycarbonyl group, an aralkyloxycarbonyl group, a nitro group, a group of formula VIIb, as defined above, or a group of formula VIc, as defined above; or
- $R_{73}$ represents a hydroxy group or a protected hydroxy group in which the protecting group is selected from substituents (b), provided that at least one of $R_{72}$, $R_{74}$ and $R_{75}$ represents a substituted alkyl group having at least one of substituents (a), a halogen atom, a hydroxy group, a substituted alkoxy group having at least one of substituents (c), a ($C_1$–$C_7$) alkanoyloxy group, a substituted ($C_2$–$C_7$) alkanoyloxy group having at least one of substituents (c), an arylcarbonyloxy group, a sulphoxy group, a ($C_1$–$C_7$) alkanoyl group, a substituted ($C_2$–$C_7$) alkanoyl group having at least one of substituents (c), a cycloalkylcarbonyl group in which the cycloalkyl part is, a substituted cycloalkylcarbonyl group in which the cycloalkyl part is ($C_3$–$C_{10}$) and has at least one ($C_1$–$C_8$) alkyl substituent, an arylcarbonyl group, a carboxy group, a ($C_2$–$C_7$) alkoxycarbonyl group, an aryloxycarbonyl group, an aralkyloxycarbonyl group, a nitro group, a group of formula VIIb, as defined above, or a group of formula VIIc, as defined above, Ar represents a divalent aromatic carbocyclic group or a divalent aromatic heterocyclic group;
- W represents a methylene group, a carbonyl group, a group of formula >CH—OY in which Y represents a hydrogen atom, a ($C_1$–$C_7$) alkanoyl group or an arylcarbonyl group, or a group of formula >C=N—OV in which V represents a hydrogen atom, a ($C_1$–$C_6$) alkyl group, a substituted ($C_1$–$C_6$) alkyl group having at least one of substituents (c), a ($C_1$–$C_7$) alkanoyl group or an arylcarbonyl group;
- U represents a single bond or a methylene group; or, when W represents a carbonyl group or said group of formula >C=N—OV, U, $R_{71}$ and the carbon atom to which $R_{71}$ is attached may together represent a group of formula —CH=C<; or when W represents a carbonyl group or said group of formula >C=N—OV, U, $R_{71}$ and the carbon atom to which $R_{71}$ is attached may together represent a group of formula —CH=C<; or W-U may represent a carbon-carbon double bond; and
- n represents an integer from 1 to 10; said aralkyl groups have an alkyl portion containing from 1 to 6 carbon atoms and an aryl portion as defined below, the alkyl portion being unsubstituted or having at least one of substituents (c);

substituents (a):
hydroxy groups; protected hydroxy groups in which the protecting group is selected from substituents (b); ($C_1$–$C_7$) aliphatic carboxylic acyl groups; ($C_2$–$C_7$) aliphatic carboxylic acyl groups having at least one of substituents (c); arylcarbonyl groups; cycloalkylcarbonyl groups in which the cycloalkyl part is ($C_3$–$C_{10}$); substituted cycloalkylcarbonyl groups in which the cycloalkyl part is ($C_3$–$C_{10}$) and having at least one ($C_1$–$C_6$) alkyl substituent; carboxy groups; ($C_2$–$C_7$) alkoxycarbonyl groups; aryloxycarbonyl groups; aralkyloxycarbonyl groups; hydroxyimino groups; protected hydroxyimino groups in which the protecting group is selected from substituents (b); groups of formula VIIB, as defined above; and groups of formula VIIc, as defined above;

substituents (b):
($C_1$–$C_6$) alkyl groups, substituted ($C_1$–$C_6$) alkyl groups having at least one of substituents (c), ($C_1$–$C_7$) aliphatic carboxylic acyl groups, substituted ($C_2$–$C_7$) aliphatic carboxylic acyl groups having at least one of substituents (c), arylcarbonyl groups, ($C_2$–$C_7$) alkoxycarbonyl groups, aryloxycarbonyl groups, groups of formula (VIIc), as defined above and sulpho groups;

substituents (c):
carboxy groups, ($C_2$–$C_7$) alkoxycarbonyl groups and aryl groups;

said aryl groups and the aryl parts of said aralkyl, arylcarbonyl, aryloxycarbonyl, aralkyloxycarbonyl and divalent aromatic groups being ($C_6$–$C_{14}$) carbocyclic aryl groups which are unsubstituted or have at least one of substituents (d);

said heterocyclic groups, heterocyclic parts of said heterocyclic acyl and acyloxy groups and said divalent heterocyclic aromatic groups have from 5 to 14 ring atoms, of which from 1 to 5 are independently nitrogen, oxygen or sulphur hetero-atoms, said heterocyclic groups being unsubstituted or having at least one substituent selected from substituents (d) and substituents (e);

substituents (d):
($C_1$–$C_6$) alkyl groups, ($C_1$–$C_6$) alkoxy groups, hydroxy groups, sulphoxy groups, halogen atoms, nitro groups, groups of formula (II), as defined above, ($C_1$–$C_7$) aliphatic carboxylic acyl groups, ($C_7$–$C_{11}$) arylcarbonyloxy groups in which the aryl part is unsubstituted or has at least one substituent selected from ($C_1$–$C_6$) alkyl groups, ($C_1$–$C_6$) alkoxy groups and halogen atoms;

substituents (e):
aryl groups and oxygen atoms. Examples of compounds containing VII are 5-[4-(6-hydroxy-2,5,7,8-tetramethylchroman-2-yl methoxy)benzyl]thiazolidine-2,4-dione (commonly known as troglitazone);

5-[4-(6-hydroxy-5,7,8-trimethylchroman-2-yl methoxy) benzyl]thiazolidine-2,4-dione; and 5-[4-6-hydroxy-5,7-diisopropyl-2-methylchroman-2-yl methoxy)benzyl]thiazolidine-2,4-dione.

The thiazolidine derivative may further be selected from compounds where X is methylene and $R_1$ is of formula VIII

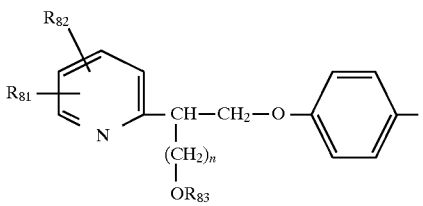

wherein
$R_{81}$ and $R_{82}$ are the same or different and each represent hydrogen or a lower alkyl group;
$R_{83}$ is hydrogen or acyl group;
n is 0 or 1. Examples include:
  5-{4-[2-(5-ethyl-2-pyridyl)-2-hydroxyethoxy]benzyl}-2,4-thiazolidinedione; and,
  5-{4-[2-hydroxy-2-(6-methyl-2-pyridyl)ethoxy]benzyl}-2,4-thiazolidinedione.

The thiazolidine dione may be further selected from compounds wherein X is a bond and $R_1$ is of formula IX

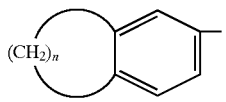

where n is an integer of 3 to 6.
Examples include:
  5-(5,6,7,8-tetrahydro-2-naphthyl)thiazolidine-2,4-dione; and
  5-(5-indanyl)thiazolidine-2,4-dione.

The thiazolidinedione may be further selected from compounds wherein Y and Z are oxo and $R_1$ is selected from compounds of the formula XI

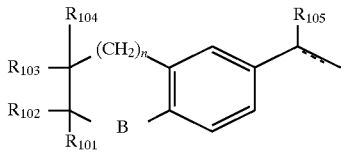

wherein the broken line is a bond or no bond, n is zero, 1 or 2; B is O,S, S=O, >S(=O)$_2$; $R_{105}$ is H, CH$_3$, or C$_2$H$_5$; when taken separately, $R_{101}$ is H, (C$_5$–C$_7$) cycloalkyl, (C$_6$–C$_8$) methyl-substituted cycloalkyl, pyridyl, thienyl, furyl, naphthyl, p-biphenylyl, tetrahydrofuranyl, tetrahydrothienyl, tetrahydropyranyl, C$_6$H$_4$W$_2$ or alk-W$_1$ and alk is (C$_1$–C$_6$) alkylene, ethylidene or isopropylidene; W$_1$ is H, OH, (C$_1$–C$_4$) alkoxy, (C$_1$–C$_4$) thioalkyl, pyridyl, furyl, thienyl, tetrahydrofuryl, tetrahydrothienyl, naphthyl, (C$_5$–C$_7$) cycyloalkyl or C$_6$H$_4$W$_2$ and W$_2$ is H, OH, F, Cl, Br, (C$_1$–C$_4$) alkyl, (C$_1$–C$_4$) alkoxy or (C$_1$–C$_4$) thioalkyl; $R_{102}$ is H or CH$_3$, $R_{103}$ is H, (C$_1$–C$_6$) alkyl, C$_6$H$_4$W$_2$ or benzyl; and $R_{104}$ is H; when $R_{101}$ and $R_{102}$ are taken together they form (C$_4$–C$_6$) alkylene and $R_{103}$ and $R_{104}$ are each H; when $R_{103}$ and $R_{104}$ are taken together they form (C$_4$–C$_6$) alkylene and $R_{101}$ and $R_{102}$ are each H; and when $R_{102}$ and $R_{103}$ are taken together they are (C$_3$–C$_4$) alkylene and $R_{101}$ and $R_{104}$ are each H.
Examples include:
  5-[(2-benzyl-2,3-dihydrobenzofuran-5-yl)methyl]thiazolidine-2,4-dione; and
  5-[(2-benzyl-3,4-dihydro-2H-benzopyran-6-yl)methyl]thiazolidine-2,4-dione (commonly known as englitazone)

and pharmaceutically acceptable salts thereof.

The thiazolidinedione may be further selected from compounds wherein Y and Z are oxo and $R_1$ is selected from compounds of the formula XII

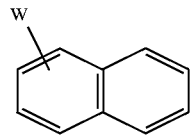

wherein W is selected from the group H, Halo, (OH)$_n$, OMe, (OCO$_2$Et)$_n$, CHalo$_3$, OCH$_2$Ph, Halo-Ph and —C$_8$H$_{17}$, where n is either 1 or 2. Preferably, formula XII is bonded to formula I at the 1 or 2 position of formula XII. When W is a Halo-Ph, formula XII is preferably bonded to formula I at the 4 position of formula XII. Br and F are preferred halogens. For example, where A and B are both H, and Y and Z are both oxo and $R_1$ is 2-naphthyl, X is preferably O, CH$_2$, CH$_2$S, CH$_2$SO$_2$, or SO. In other examples, wherein A and B are both H and Y and Z are both oxo, and X is SO$_2$, $R_1$ is 4-Br-phenyl, 4-F-phenyl, or n-octyl. In the example just described, where $R_1$ is n-octyl, X can be S instead of SO$_2$.

Some examples of 1-naphthalenyl analogs having $R_1$ of formula XII include the following: Y and Z are both oxo, X is SO$_2$, A is H, B is H and W is either 5-Br, H, 5-CF$_3$ and 6-OMe, or 8-OMe. Where the compound is as just described but B is a methyl instead of an H, W is 5-Br. In other examples, X, Y, and Z are as above, A and B are both methyls, and W is 5-Br. Another example has X, Y, Z and A as above, B is H and W is also H.

Definitions
Thiazolidine refers to an organic compound containing a derivatized thiazole ring system.

Carbocyclic describes a homocyclic ring compound in which all the ring atoms are carbon, e.g., benzene.

Heterocyclic refers to a ring compound having atoms other than carbon in its nucleus, e.g, pyrrole or thiophene.

Alkylidene, C$_n$H$_{2n}$, refers to a divalent organic radical derived from an aliphatic hydrocarbon, e.g., ethylidene in which two H atoms are taken from the same C atom.

Oxo is a prefix indicating the =O group as in aldehydes and 2-oxopropanoic acid.

Imino is a prefix indicating the =NH group attached to one or two carbon atoms; as =C:NH or —C—NH—C—.

Benzyl or phenylmethyl is an aryl radical derived from toluene.

Alkyl, C$_n$H$_{2n+1}$—, refers to a monovalent radical derived from an aliphatic hydrocarbon and designated by the number of carbon atoms, e.g., methyl, ethyl, propyl, etc.

Cycloalkyl is the generic name for radicals derived from cycloalkanes, e.g., cyclohexyl.

Phenyl refers to the radical C$_6$H$_5$— from benzene.

Methylene refers to the groups —CH$_2$— and =CH$_2$.

Oxazole refers to a liquid with formula C$_3$H$_3$ON.

Thiazole is a heterocyclic, colorless liquid of formula C$_3$H$_3$NS.

Alicyclic refers to the group of cyclic organic compounds derived from the corresponding aliphatic compounds by ring formation and having a saturated ring such as the cyclopariffins.

Acyl refers to an organic radical derived from an organic acid by removal of the hydroxyl group; e.g., R—C(O)— is the acyl radical of R—COOH. They are named by number of carbons; formyl, acetyl, propynyl, etc.

Alkoxy designates an alkyl radical attached to a nucleus through an oxygen, e.g., methoxy.

Aryl is an organic radical derived from an aromatic hydrocarbon by removal of one hydrogen, e.g., phenyl from benzene.

Alkylene is an alkene radical, $C_nH_{2n-1}$, as in ethylene.

Dioxy is a suffix indicating a —O—R—O— radical, where R is a bivalent radical such as carbonyldioxy, —O—CO—O—.

Alkylcarboxy designates a radical of the general formula R—C—, where R is an alkyl group.

Aralkyl is an arylated alkyl or a radical in which an alkyl H atom is substituted by an aryl group.

Carboxy or carboxyl is a prefix indicating the acidic group —COOH.

Sulfo is a prefix designating the sulfonic acid group, —SO$_3$H or the presence of divalent sulfur.

Nitro is a prefix denoting the radical —NO$_2$.

Halo is a prefix indicating the presence of a halogen, e.g., fluoro, chloro, bromo, etc.

"Me" means methyl, "Et" means ethyl, and "Ph" means phenyl.

Protecting group here refers to any chemical group bonded to a functional group so as to eliminate its reactivity for a particular process.

Unless otherwise stated all carbon numbers ($C_x$–$C_y$) are inclusive. Where two carbon containing moieties are provided, such as alkylcarboxy of 1–7 carbons, the carboxy is included as a carbon of the 1–7. Thus, both formyl and hexylcarbonyl are embraced by the term alkoxy of 1–7 carbons. Similarly, where "n" is an integer, the numbers are inclusive. That is, the phrase "where n is an integer from 1 to 3" means that n can be 1, 2 or 3.

Where asymmetric carbon atoms are present, all stereoisomeric forms are intended.

The terms "treatment", "therapy" and the like refer to improvement in the recipient's status as well as prophylaxis. The improvement can be subjective or objective and related to features such as symptoms or signs of the disease or condition being treated. Prevention of deterioration of the recipient's status is also included by the term.

The terms "symptoms" and "signs" can overlap. For example, if the patient notes a decreased frequency or duration of skin lesion recurrences (improved symptoms), then treatment has been successful. Similarly, if the clinician notes objective improvement such as fewer skin lesions (improved signs), then treatment has also been successful.

The term "ameliorate" or "amelioration" includes any of the arrest, prevention, decrease, and improvement in any of the symptoms, signs, and features of the disease being treated, both temporary and longterm. Thus, amelioration of any aspect of a disease is an example of successful treatment.

The terms "cellular material," "cellular sample" and "tissue" refer to animal tissue, cells or portions thereof which can include, for example, whole cells, parts of cells, extracellular material and lysates of cells. The term "tissue" embraces extracellular material and acellular material of animal origin. A biopsy sample is an example of tissue or cellular material.

The compounds generally fall into the family of compounds of formula I which is then subdivided into several genera. Unless otherwise limited, the symbols are as previously defined. The following provides general guidance for the organic synthesis of compounds of the various formulae described herein.

2. Synthesis of Therapeutic Compounds

A. Synthesis of Thiazolidine Ring and Substituents

Compounds having the general structural formula I:

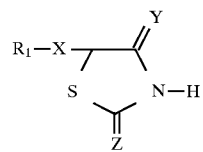

can be synthesized by a variety of methods depending on the availability of starting compounds. The parent heterocyclic ring structure of formula I can be synthesized by the following reaction scheme which is found in the method of Kawamatsu, U.S. Pat. No. 4,486,594, and incorporated by reference herein.

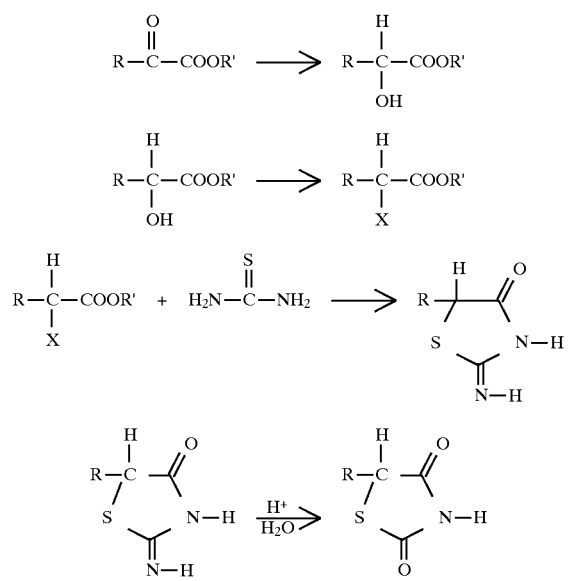

R represents any of the substituents of $R_1$;
R' can be hydrogen, alkyl or aralkyl and X stands for a group to be eliminated.

Reaction 3) above yields a product where substituent Z from general formula (I) is imino. Therefore, reaction 4) is optional depending on the product desired.

Where it is desired to have substituent Y from general formula (I) to be an imino group, the following modifications can be used:

Start with a compound of the formula:

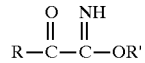

and proceed through steps 1) through 4) above.

Alternatively one may follow the method of Yoshioka et al., U.S. Pat. No. 4,572,912, which is incorporated by reference herein. To synthesize the thiazolidine ring begin with a compound of formula:

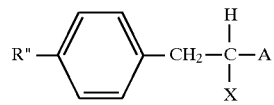

where substituent R" is any of the $R_1$ substituents of formula I (preferably the substituent represented by formula VI), where X is a halogen and where A is a cyano group. There is produced an imino substituent at the carbon at position 4 of the ring and where A is a carboxy, alkoxycarbonyl, an oxygen substitution will be effected at position 4 of the ring. Compound 3 can be reacted with thiourea in a reaction analogous to reaction 3) above to yield the following:

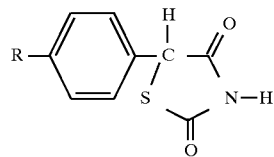

Details of the steps for the synthesis of the general compounds illustrated above will vary according to the nature of the $R_1$ groups in the general formula of I. In some instances, blocking groups are useful to prevent unwanted side reactions. At times the nature, pH, and temperature of solvent mixtures may be variable for the same reason, but the following general conditions apply to the synthetic scheme illustrated in reactions 1) through 4) above.

Reaction 1) is the reduction of the keto acid to the corresponding secondary alcohol. The reductant can be lithium aluminum hydride or sodium bis(2-methoxyethoxy) aluminum hydride. This reaction is preferably conducted in the presence of some solvent, the nature of which is not critical, provided that it does not interfere with the reaction. Suitable solvents include ethers, aromatic hydrocarbons and aliphatic hydrocarbons. It is preferable to use a ratio of reductant to keto acid of from one to two moles reductant per mole of keto acid. The reaction is generally carried out at 10° to 100° C. for a period from ten minutes to twenty hours.

Reaction 2) can be either a halogenation or sulfonylation of the product of reaction 1).

Halogenation is carried out by reacting a halogenating agent such as phosphorus tribromide, thionyl chloride or phosphorus oxychloride with the product of 1) in the presence or absence of a solvent such as dichloromethane or chloroform. The reaction is preferably conducted at an elevated temperature, for example 20° to 100° C.

Sulfonylation of the product of reaction 1) can be conducted by reacting the compound with sulfonylating agent, e.g. mesyl chloride, tosyl chloride or benzenesulfonyl chloride at 0° to 60° in a suitable solvent, e.g. benzene, ethyl acetate, dichloromethane or chloroform in the presence of a base such as pyridine or triethylamine.

The reaction of the compound formed in 2) is then allowed to react with thiourea usually in a solvent exemplified by alcohols, ethers, acetone, dimethylformamide, dimethylsulfoxide or sulfolane. The amount of thiourea is preferably 1–2 moles per mole of reaction 2) product. The reaction temperature is preferably 60° to 130° C.

If desired the compound of reaction 3) can then be hydrolyzed by heating in a suitable solvent such as sulfolane in the presence of water and a mineral acid. The acid is added in a proportion of preferably 0.2 to 3.0 equivalents per equivalent of reaction 3) product. Water is normally in large excess. Heating time ranges from 2–10 hours.

The object-compound of formula I can be isolated and purified by a conventional means such as concentration, solvent extraction, recrystallization, chromatography or the like. The object compound which may be an acid compound may be converted to a salt with, for example, alkali metal, alkaline earth metals, or organic bases such as sodium, potassium, calcium, amines and the like.

An alternative methodology for the formation of the starting compound (I) starts with a compound of R—OH where R corresponds to the $R_1$ of formula I absent an aryl moiety and are preferably compounds of formula IV. The alcohol is reacted with p-nitrofluorobenzene as illustrated below according to the method of Meguro et al., U.S. Pat. No. 4,775,687.

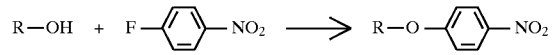

This reaction serves the advantage of allowing the aryl group to be added synthetically if it is not available in the $R_1$ moiety of formula I. Following the formation of the product of reaction 5), the following successive steps are taken:

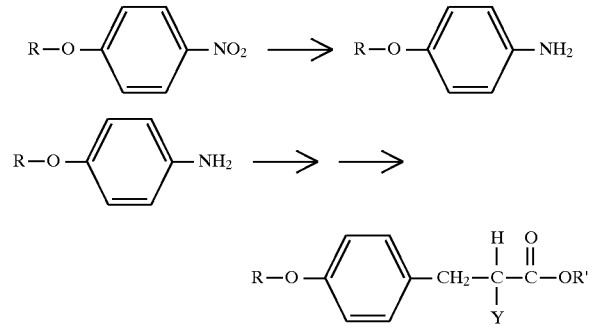

where Y is a halogen.

The product of reaction 7) is then available for reaction with thiourea as previously described in reaction 3).

Reaction 5) is a condensation in the presence of sodium hydride. The reaction can be performed in a solvent such as dimethylformamide or tetrahydrofuran at −10° to 20° C. Subsequently, reaction 6) can be carried out, for example, by subjecting the product of reaction 5) to catalytic reduction with palladium carbon as a catalyst. The product of reaction 6) then undergoes the so-called Meerwin arylation. It is diazotized in the presence of a hydrohalic acid (HY) and then reacted with acrylic acid or an ester thereof in the presence of a copper catalyst, e.g. Cu(I) oxide, CU(II) oxide, Cu(I) chloride or CU(II) chloride.

B. Synthesis of Various Thiazolidine Derivatives Where $R_3$ is substituted by substituents represented by formulae IIb-d.

The following groups of compounds are each derivatives of the compound designated (I) above. The R group is variable and the synthesis of each will vary according to the chemical moieties desired.

1. Compound of formula IIa

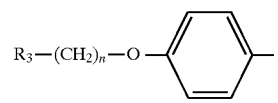

n is a methylene bridge of 1–4 carbons and $R_3$ is a compound of formula IIb, IIc or IId.

To provide compounds of formula IIa where $R_3$ is IIb, one may use the reaction sequence according to the method of Meguro et al., U.S. Pat. No. 4,812,570, which is incorporated herein by reference and consists of the following steps:

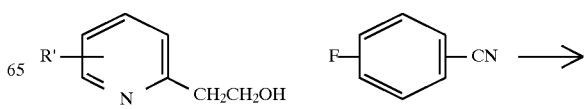

-continued

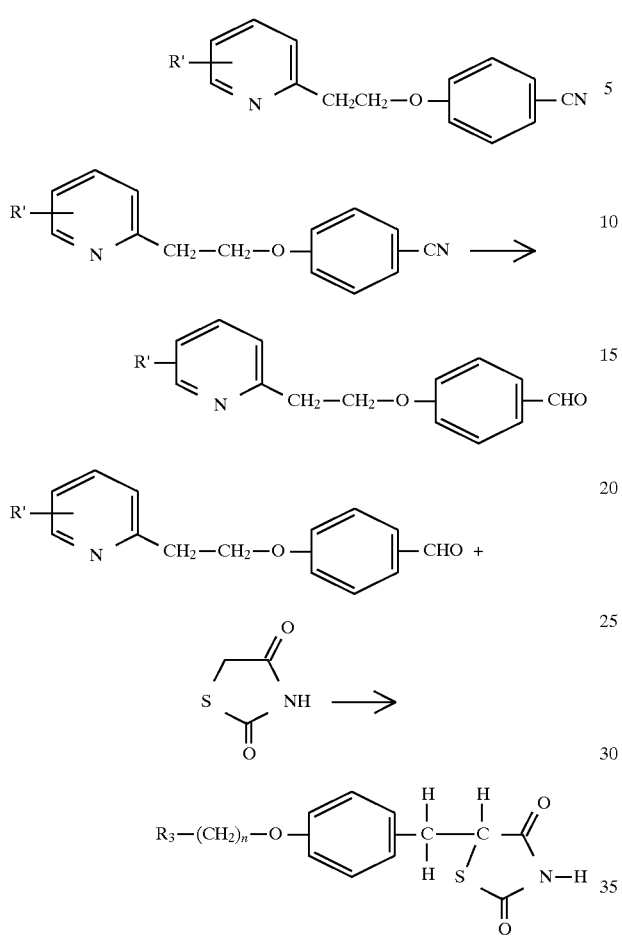

The specific conditions for the reaction sequence above involve first condensing the reactants of step 1) above in the presence of, for example, sodium hydride. The reaction is preferably conducted in a solvent such as dimethylformamide, dimethylsulfoxide, tetrahydrofuran or dimethoxyethane at −10° to 30° C.

The reaction step 2) is effected by heating the product of reaction 1) together with Raney nickel alloy in aqueous formic acid. The product of reaction 2) reacts with the thiazolidinedione ring in a suitable solvent-base system. Suitable solvents include short chain alcohols, dimethylformamide, dimethylsulfoxide, sulfolane, acetonitrile, dioxane, dimethoxyethane or acetic acid. Appropriate bases include ammonia, amines (for example, methylamine, ethylamine, n-butylamine, pyrrolidine, piperidine, morpholine, piperazine, diethylamine, diisopropylamine or triethylamine), sodium alkoxides (for example, sodium methoxide or sodium ethoxide), alkali metal carbonates, sodium hydroxide, sodium acetate, an so on. The thiazolidine ring compound is used in a proportion of 1 to 2.5 moles per mole of the product of reaction 2). The base is generally used in a proportion of 0.3 to 0.5 moles per mole of the product of reaction 2). This condensation reaction is generally conducted at 40° C. to reflux temperature and preferably at 60° to reflux temperature for 0.5 to 50 hours.

The thiazolidinedione ring reactant in step 3) is made according to the procedure detailed in part A above.

2. To provide compounds of formula IIa where R3 is IIc, one may use the reaction sequence according to the method of Kawamatsu et al., U.S. Pat. No. 4,461,902, which is herein incorporated by reference. The alpha-halocarboxylic acids used as starting materials in the production of the cyclohexyl-derivatized thiazolidines are synthesized by steps identical to those shown in reactions 5) through 7) above but where the compound reacting with p-nitrohalobenzene is:

In cases where the cyclohexane ring of the thus-obtained thiazolidine derivatives has a hydroxyl group substitution at one of the methylenes, such compounds may further be converted to those compounds which have an oxo group as a substituent on the cyclohexane ring by oxidation, while those compounds which have an oxo group on the cyclohexane ring may be converted to the corresponding hydroxyl compounds by reduction. Preferable oxidizing agents are of the chromium trioxide species (e.g. Jones' reagent, chromium trioxide-pyridine) and preferable reducing agents are sodium borohydride and aluminum isopropoxide-isopropanol.

3. To provide compounds of formula IIa where $R_3$ is IId,

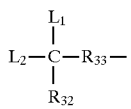

one may use the reaction sequence according to the method of Kawamatsu et al., U.S. Pat. No. 4,444,779, which is herein incorporated by reference. The reaction is as follows:

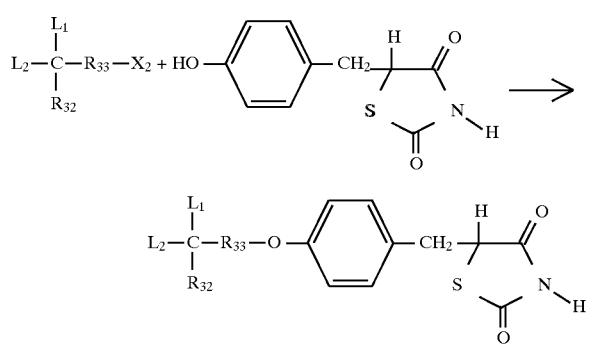

where the substituents are as defined earlier, except that $X_2$ is a halogen atom.

The above reaction will take place in the presence of a base such as sodium hydride, potassium carbonate, sodium carbonate, potassium hydroxide or sodium hydroxide in the presence of a solvent such as dimethylformamide or dimethylsulfoxide at 20° to 100° C.

C. The Synthesis of compounds of formula I where $R_1$ is substituted by radicals of formula IV.

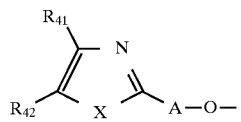

To obtain compounds of formula I where $R_1$ is substituted by radicals of formula IV, one may use the methods of synthesis detailed in the work of Meguro et al., U.S. Pat. No.

4,775,687, which is incorporated herein by reference. Two alternative methods are available.

First, if the starting materials are conveniently available, the compound can be synthesized directly by the reaction:

4. To provide compounds of formula Ia where $R_3$ is IIf, one may use the reaction sequences according to Hindley, U.S. Pat. No. 5,002,953, which is herein incorporated by reference.

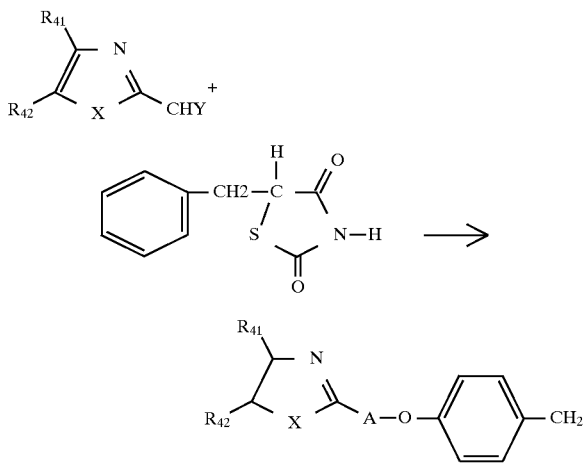

The above reaction is carried out in the presence of a base in an appropriate solvent. Examples of said base are sodium hydride, potassium hydride, sodium amide, sodium alkoxide (e.g. methoxide or ethoxide), potassium alkoxide (e.g. potassium t-butoxide) and potassium carbonate. Solvents include among others dimethylformamide, dimethylsulfoxide, sulfolane, tetrahydrofuran and dimethoxyethane. The reaction is preferably carried out by first allowing formation of a dianion by bringing such base into contact with the thiazolidine derivative in a molar ratio of 2:1 and thereafter adding the other reactant in an amount equimolar with the thiazolidine derivative. This condensation reaction is carried out preferably at 20° to 100° C. for 0.5 to 5.0 hours.

Alternatively, the starting compound containing the R group illustrated above (preferably where X is oxygen) can be produced by the following method:

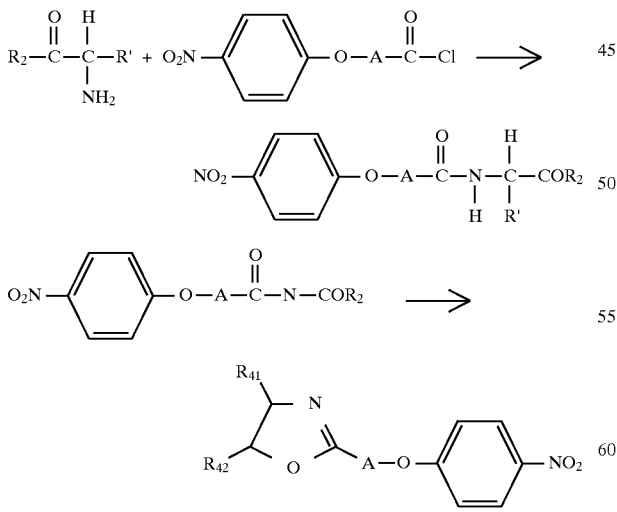

These two reactions are followed by the series of steps previously detailed previously as steps 6) and 7) of part A. The product of reaction 7) is then available for reaction with thiourea as previously described.

Reaction 1) above is a condensation in the presence of a deacidifying agent (e.g. potassium carbonate, sodium carbonate, sodium bicarbonate, potassium bicarbonate, sodium hydroxide, potassium hydroxide or triethylamine) in a solvent such as dimethylformamide, dimethylsulfoxide, tetrahydrofuran, ethyl ether, ethyl acetate, chloroform or dichloromethane, or a mixed solvent prepared by adding water to such solvent as necessary at −10° to 50° C.

The product of reaction 1) is subjected to ring closure (reaction 2). This reaction is carried out in the presence of a dehydrating agent such as phosphorus oxychloride, thionyl chloride, phosphorus pentoxide, polyphosphoric acid, polyphosphoric acid esters, acetic anhydride or sulfuric acid, or mixtures of these. This reaction generally can be effected in an inert solvent (e.g. benzene, toluene, xylene, dichloromethane or chloroform) at about 30° to 140° C. or in an excess of dehydrating agent which serves also as a solvent within said temperature range. The dehydrating agent is used in an amount of 1–30 moles per mole of reactant.

D. The Synthesis of compounds of formula I where $R_1$ is substituted by radicals of formula V.

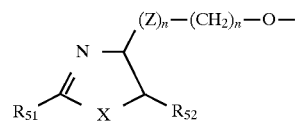

To obtain compounds of formula I where $R_1$ is substituted by radicals of formula V, one may use the methods of synthesis detailed in Meguro et al., U.S. Pat. No. 4,725,610, which is incorporated herein by reference. The steps of the synthesis of the starting compound are as follows:

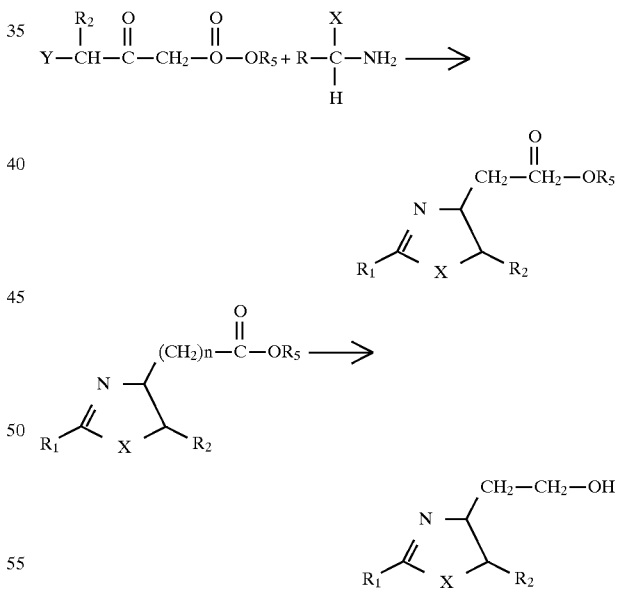

Where Y is a halogen of chlorine, bromine or iodine and $R_5$ is hydrogen or a lower alkyl.

The product of either reaction 1) or 2) above may be used as a reactant either in the sequence of steps detailed earlier as 5) through 7) or, alternatively, through reaction sequence 1) through 3) as described for Compound 1 to produce the derivatized thiazolidine.

Reaction 1) above is easily conducted in a alcohol solvent such as methanol, ethanol, propanol, etc. or without a solvent by heating to about 40° to 150° C.

The product of reaction 1) is reduced in a conventional method, for example, using lithium aluminum hydride.

E. The Synthesis of compounds of formula I where $R_1$ is substituted by radicals of formula VI.

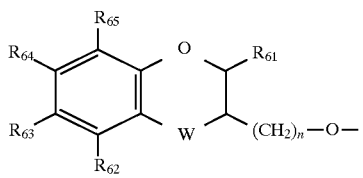

To obtain compounds of formula I where $R_1$ is substituted by radicals of formula VI, one may use the methods of synthesis detailed in Yoshioka et al., U.S. Pat. No. 4,572,912, which is incorporated herein by reference. Yoshioka provides two alternative methods to generate the compounds of this family.

Method A—(If the starting compound is available):

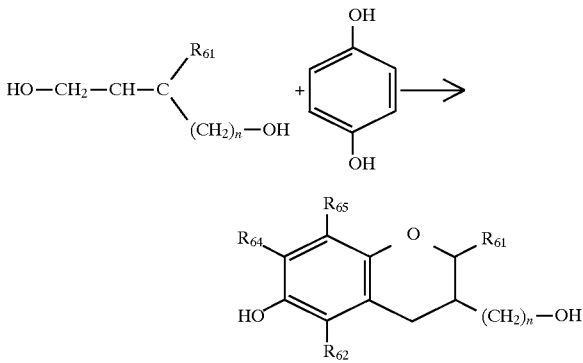

as described in West German Pat. No. 3,010,504, in the presence of aluminum chloride. The product of this reaction is then taken through the steps detailed earlier as reactions 5) through 7).

Method B—(If the starting compound is available):

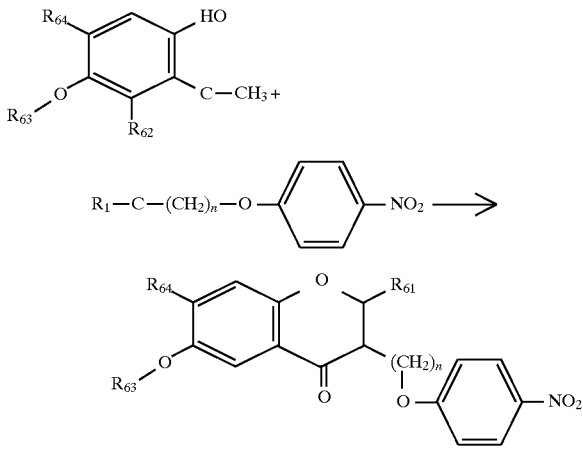

The acetophenone derivative reactant above may be prepared, for example, as described in Chem. Berichte 95: 1413. The other starting compound, p-nitrophenoxyalkyl alkyl ketones, may be prepared, for example, as described in J. Med. Chem. 21: 386 (1978). The reaction takes place in the presence of a secondary amine and preferably in a suitable solvent which may include aliphatic and aromatic hydrocarbons such as petroleum ether, benzene, toluene, xylene, hexane or cyclohexane; halogenated aliphatic and aromatic hydrocarbons such as carbon tetrachloride, methylene chloride, chloroform, chloro- and dichlorobenzene; ethers such as diethyl ether, tetrahydrofuran and dioxane; amides such as dimethylformamide, dimethylacetamide and N-methylpyrrolidone; alcohols such as reethanol, ethanol and ethylene glycol monomethyl ether; esters such as ethyl acetate; nitriles such as acetonitrile; and sulfoxides such as dimethylsulfoxide.

Examples of preferable secondary amine catalysts include diethylamine, dimethylamine, N-methylpiperazine, pyrrolidine, piperidine or morpholine, of which pyrrolidine is particularly preferred.

The molar ratio of reactants is not particularly critical, but to avoid waste roughly equimolar amounts are used. The amount of secondary amine is preferably from 0.1 to 1.0 mole per mole of reactant.

In general it is preferred to carry out the reaction at a temperature of from 10° to 120° C. for a period from 30 minutes to three days.

Formulations of compound VI in which W is hydroxy substituted methylene, >C—OH, may be prepared by reducing the corresponding compound in which W is oxy substitute methylene, >C=O.

The reducing agent for this reaction is any one which is capable of reducing a ring carbonyl group to a hydroxy group without affecting the remainder of the molecule. Suitable reducing agents include borohydrides, especially sodium borohydride. Preferably one employs an excess of reductant of from one to 20 moles per mole of the other reactant. The reaction is preferably carried out at 0° to 100° for from one to twenty hours.

F. The Synthesis of compounds of formula I where $R_1$ is substituted by radicals of formula VII.

To obtain compounds of formula I where $R_1$ is substituted by radicals of formula VII, one may use the methods of synthesis detailed in the work of Horikoshi et al., EPO 0277836, which is herein incorporated by reference.

One means of synthesizing thiazolidine derivatives containing the structure depicted above entails the direct reaction of

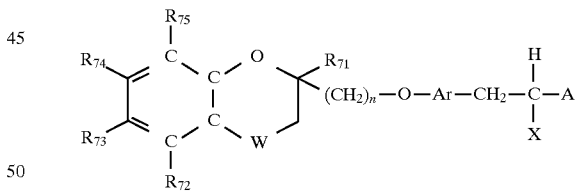

where X represents a halogen and A represents cyano, carboxy, or $C_2$–$C_6$ alkoxycarbonyl with thiourea analogously to steps 3) and 4) in Part A. Where such a starting compound is unavailable, it may be synthesized according to the method of Horikoshi et al., EPO 0277836, and as presented below.

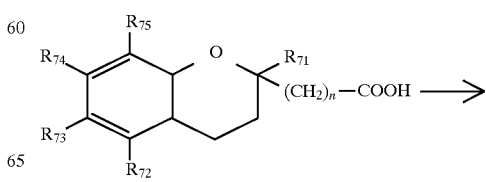

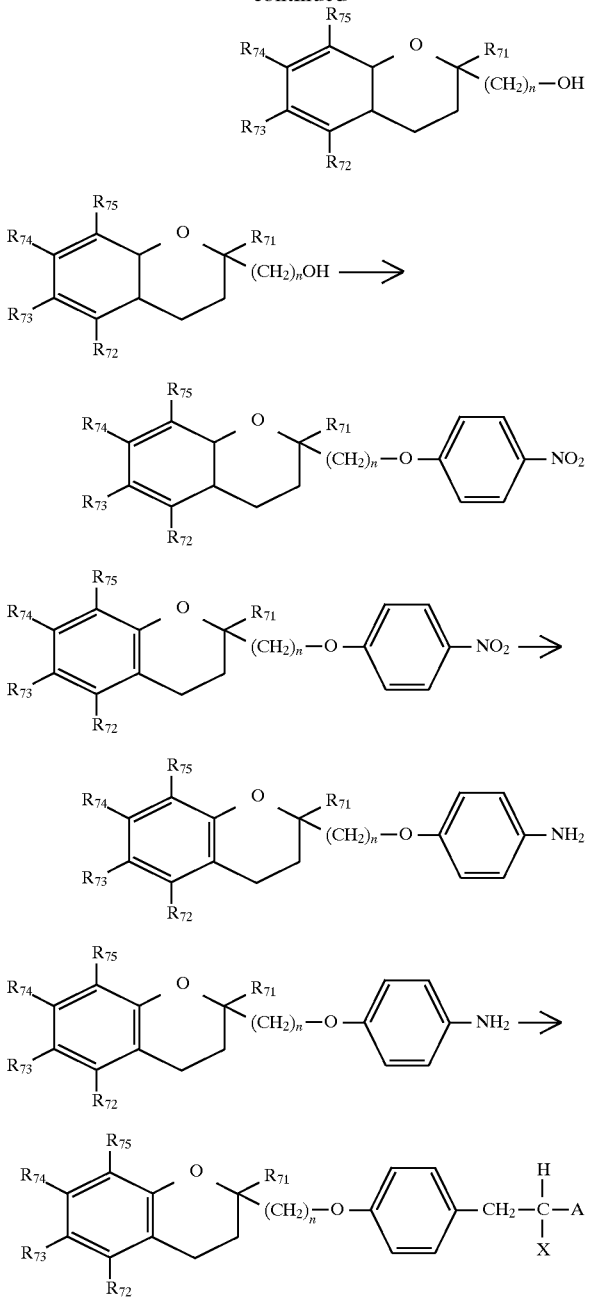

Reaction 2) involves the same chemistry as reaction 5) of the process depicted in Part A.

In step 2) it is preferred that any free hydroxy group which is a ring substituent be protected. Examples of suitable protecting groups include optionally substituted alkyl groups such as methoxymethyl and 2-tetrahydropyranyl groups.

In step 3) it is preferred to protect any amino group with suitable protecting groups including alkoxycarbonyl groups, such as methoxycarbonyl or ethoxycarbonyl groups.

In addition when synthesizing the product of reaction 3), if the product of reaction 2) is substituted by a hydroxy group protected by any one of the alkyl groups mentioned above or is substituted by a hydroxy-containing group protected by any one of the alkyl groups mentioned above, the protected group may be removed and the resulting hydroxy group may be protected again with another group, for example, an acyl group, such as an acetyl or benzoyl group.

Step 3) is a reduction of the product of step 2); a similar reaction may be carried out to convert nitro substituents on these compounds to amino groups which can then be protected as mentioned above.

The reduction steps, 1) and 3), may be a catalytic reduction process employing hydrogen or reduction with a metal, such as zinc or iron, and an acid (which may be a mineral acid, such as hydrochloric acid or sulfuric acid, or an organic acid, such as acetic acid. The preferred catalyst is palladium on carbon, Raney nickel or platinum oxide. The hydrogen pressure is preferably from one to six atmospheres (1.01 to 6.06 bars). The reaction is preferably conducted in a solvent having no adverse effect on the reaction. Examples of suitable solvents include alcohols, such as methanol or ethanol; aromatic hydrocarbons such as benzene or toluene; organic acids such as acetic acid; amides such as dimethylformamide; water; or a mixture of any two or more of the above.

The reaction conditions may vary depending on the chemical nature of the starting material, the method employed for reduction or the solvent, but is normally effected at 20° to 50° C. for from several minutes to 50 hours.

Reaction 4) is the same process detailed above as an alternative method for generating compound (I). See step 7).

If unavailable, the starting compound for step 1) above may be synthesized beginning with a phenol in the following reaction:

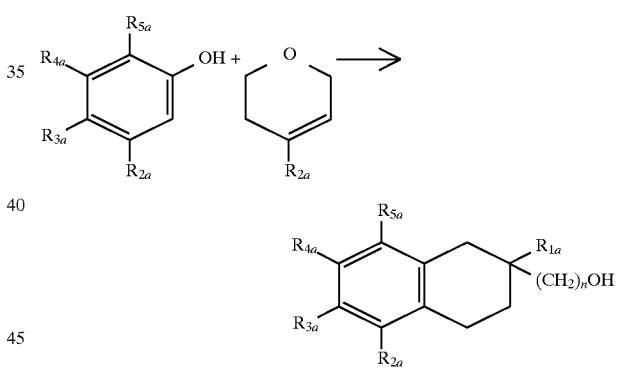

This reaction generates the same product as that of step 1) above. The reaction conditions are described in Japanese Pat. Application Kokai No. 201775/83.

G. The Synthesis of compounds of formula I where $R_1$ is substituted by radicals of formula VIII.

To obtain compounds of formula I where $R_1$ is substituted by radicals of formula VIII,

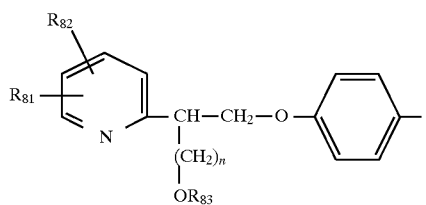

one may use the methods of synthesis detailed in Meguro et al., U.S. Pat. No. 4,582,839, which is incorporated herein by reference. Starting with a compound illustrated as:

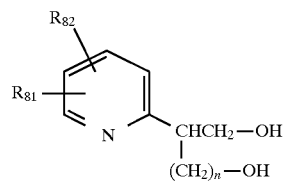

it is taken through an analogous reaction sequence detailed earlier as steps 5), 6) and 7) for the production of compound (I). At this point the product of reaction 7) will be

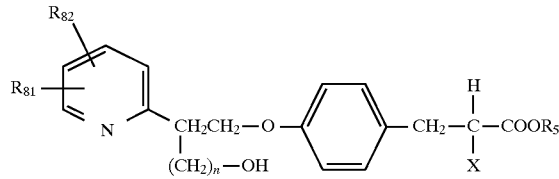

where R' is a lower alkyl of 1 to 4 carbons and said ester can be acylated by the following reaction:

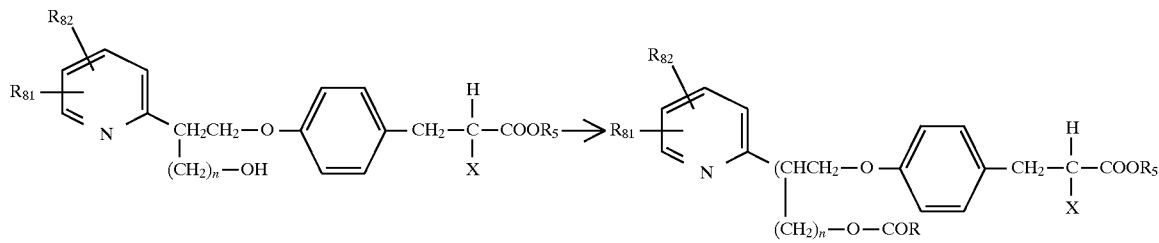

This acylation is easily conducted by heating with an acid halide or acid anhydride 80° to 150° C.

This product is then available to react with thiourea as previously described to form the thiazolidine derivative.

H. The Synthesis of compounds of formula I where $R_1$ is substituted by radicals of formula IX.

To obtain compounds of formula I where $R_1$ is substituted by radicals of formula IX, one may use the methods of synthesis detailed in Meguro et al., U.S. Pat. No. 4,486,594

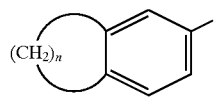

which is incorporated herein by reference. Starting with a compound illustrated as:

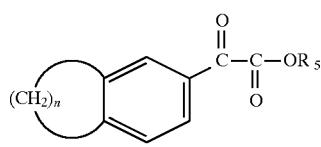

where $R_5$ is a lower alkyl of 1–4 carbons and proceeding analogously through the steps 1) through 3) as detailed for the compounds of formula I described above in part A.

I. The Synthesis of compounds of formula I where $R_1$ is substituted by radicals of formula XI.

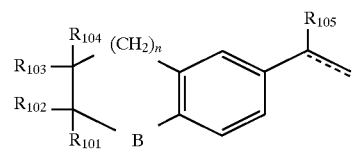

The compounds of formula XI are prepared, for example, by the method illustrated below as detailed in Eggler et al., U.S. Pat. No. 4,703,052 which is incorporated herein by reference.

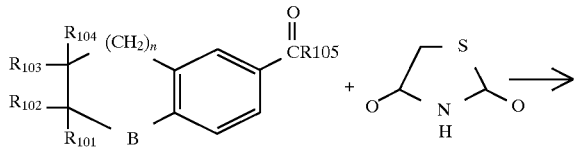

-continued

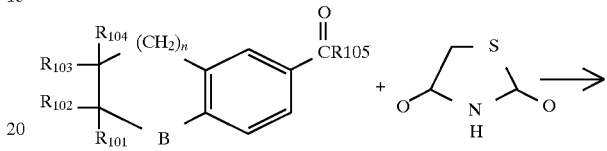

In the first step of the above synthetic scheme, approximately equimolar amounts of the carbonyl reactant and the thiazolidinedione are heated in the presence of a mild base to provide the olefin product. While this step may be carried out in the presence of a reaction-inert solvent, it is preferably carried out in the absence of solvent at a temperature which is sufficiently high to cause at least partial melting of the reaction mixture. A preferred temperature is in the range of from 100° to 250° C. Especially preferred is a temperature of from 140° to 200° C.

Examples of suitable mild bases for the above reaction include the alkali metal and alkaline earth salts of weak acids such as the ($C_1$–$C_{12}$) alkyl carboxylic acids and benzoic acid; alkali metal and alkaline earth carbonates and bicarbonates such as calcium carbonate, magnesium carbonate, potassium bicarbonate; and tertiary amines such as pyridine, N-methylmorpholine, N-ethylpiperidine and the like. A more preferred mild base is sodium acetate for reasons of economy and efficiency.

In a typical reaction, the aldehyde or ketone starting material and thiazolidinedione are combined in approximately equimolar amounts with a molar excess, preferably a 2–4 fold molar excess, of anydrous sodium acetate and the mixture is heated at a temperature high enough to effect melting, at which temperature the reaction is substantially complete in from about 5 to 60 minutes. The desired olefin is then isolated, for example, by mixing with water and filtration, to obtain the crude product, which is purified, if desired, e.g., by crystallization or by standard chromatographic methods.

The olefinic product of step 1 serves as intermediate for preparation of the corresponding reduced compound shown as the product of step 2. The reduction of the above olefin may be carried out by employing a wide variety of reducing agents which are known to reduce carbon-carbon double bonds. However, since hydrogenation methods have a well-known tendency to cleave benzylic carbon-oxygen bonds a preferred method for reduction of the compounds of the olefin is conventional sodium amalgam reduction in methanol, usually at or about ambient temperature.

When the reduction is substantially complete, the desired product of formula XI is then isolated by filtration, the solvent evaporated and the product purified, if desired, by well known methods such as crystallization or by chromatography.

The reactions employed to prepare the compounds of this invention can generally be monitored by standard TLC methods, employing commercially available plates. Suitable eluants are common solvents such as chloroform, ethyl acetate or hexane or suitable combinations thereof which will differentiate starting materials, products, by-products, and in some cases intermediates. Applying these methods, which are well-known in the art, will permit further improvement in the methodology of selection of more optimal reaction times and temperatures.

The requisite 2,3-dihydrobenzofurans, 2,3-dihydrobenzothiophenes, chromans, thiochromans, tetrahydrobenzooxepins and tetrahydrobenzothiepins, as well as the corresponding bromo-substituted and hydroxyalkyl-substituted compounds which are precursors of the starting aldehydes and ketones of are prepared by a variety of methods known in the art. A process for preparing one simple aldehyde is illustrated below. The preparation of other aldehydes can be found in U.S. Patent No. 4,703,052 (Examples 1–9) which is incorporated by reference herein.

J. General Method for Preparation of Aldehyde Starting Compounds 5-Formyl-2,3-dihydrobenzofuran.

A solution of 9.4 ml (83.4 mmole) 2,3-dihydrobenzofuran in 250 ml methylene dichloride was cooled under nitrogen to 0° to –5° C. and 18 ml (167 mmole) titanium tetrachloride was added dropwise at 0° C. The resulting brown mixture was stirred 10 minutes and 8.3 ml (91.6 mmole) 1,1-dichloromethyl methylether was then added dropwise at 0° C. During this addition the reaction mixture became dark red. The mixture was allowed to warm to room temperature, stirred for two hours and poured slowly into a 2 liter beaker containing 700 ml saturated aqueous sodium bicarbonate solution. The resulting mixture was filtered through diatomaceous earth and the solids washed with methylene dichloride. The separated organic layer was dried ($Na_2SO_4$) and the solvent evaporated to afford a residual oil, 10 g (81%) of which appeared homogeneous on silica gel TLC, eluting with an ethyl acetate/hexane/5% acetic acid 1:5:5 by volume. Mass spectrum (m/e): 148 (M+), 147, 119.

K. The Synthesis of compounds of formula I where $R_1$ is substituted by radicals of formula XII.

An efficient one-step route to the sulfonyl-2,4-thiazolidinediones employed a selective C-5 sulfonylation of dilithio-2,4-thiazolidinedione upon treatment with a sulfonyl chloride is presented (Scheme I). See Zask, et al., *J. Med. Chem.* 33: 1418–1423 (1990), from which the following syntheses for compounds of formula XII are taken and which is incorporated herein by reference. The dianion was readily prepared by the treatment of 2,4-thiazolidinedione with 2 equivalents of n-butyllithium. An alternative two-step sequence utilized a base-mediated coupling of a thiol with 5-bromo-2,4-thiazolidinedione to provide the 5-thio intermediate, which was oxidized to the sulfone with an excess of hydrogen peroxide in acetic acid (Scheme I).

Scheme I

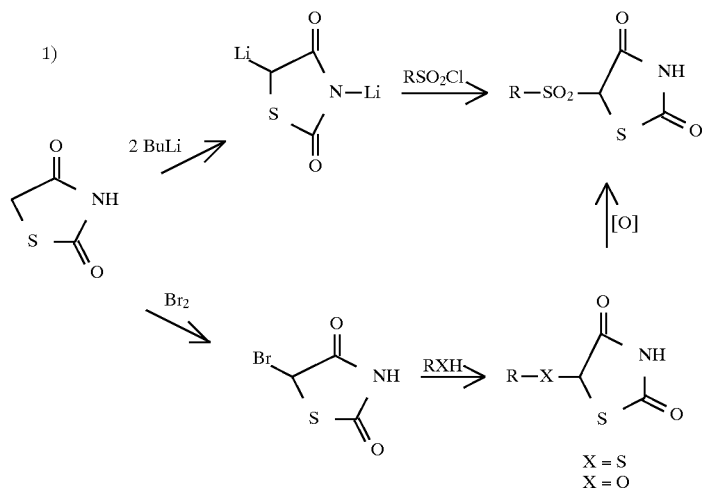

X = S
X = O

Scheme II

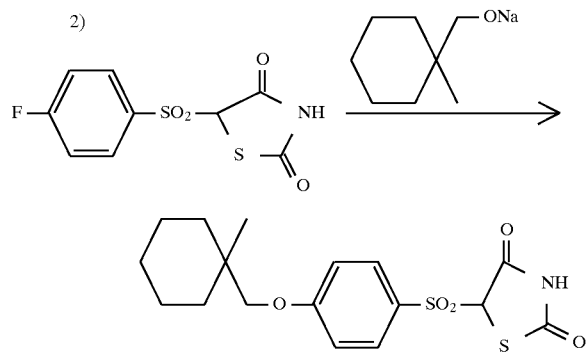

The requisite 5-bromo-2,4-thiazolidinedione was obtained by bromination of 2,4-thiazolidinedione with bromine in acetic acid. In an analogous reaction, coupling of 2-naphthol with the thiazolidinedione in the presence of base gave the corresponding ether. Selective oxidation of the sulfide to the corresponding sulfoxide was effected by treatment with 1 molar equivalent of m-chloroperbenzoic acid.

Selective N-methylation of the 2,4-thiazolidinedione ring was accomplished by treatment of naphthalene sulfone analogue with equimolar amounts of sodium hydride and iodomethane. Dimethylation of the sulfone took place upon treatment with excess potassium carbonate and iodomethane. The C-5 methyl analogue was synthesized by preparation of the dianion of 5-methyl-2,4-thiazolidinedione followed by treatment with 1-naphthalenesolfonyl chloride.

A route to the 4-alkoxyphenyl sulfone analogue bearing the lipophilic alkoxy group found in ciglitazone utilized a nucleophilic displacement of fluoride from 5-[(fluorophenyl)sulfonyl]-2,4-thiazolidinedione by the alkoxide of (1-methylcyclohexyl)methanol (Scheme II). Treatment of the thiazolidinedione with (1-methylcyclohexyl)methanol in dimethyl-formamide in the presence of sodium hydride gave the desired analogue.

Method A. 5-[(Bromo-1-naphthalenyl)sulfonyl]-2,4-thiazolidinedione. To a stirred solution of 2,4-thiazolidinedione (5.5 g, 47 mmol) in tetrahydrofuran (THF) (275 mL) at $-78°$ C. under nitrogen was added n-butyllithium (62 mL, 99 mmol) portionwise over 15 minutes. The mixture was maintained at $-78°$ C. for 15 minutes and then warmed to $0°$ C. for 30 minutes to complete the dianion formation. Upon recooling to $-78°$ C., 5-bromo-1-naphthalene-sulfonyl chloride (16 g, 52 mmol) was added as a solid, all at once. After 30 minutes the solution was allowed to warm to $25°$ C. After 1.5 hours the reaction mixture was treated with 5% aqueous sulfuric acid. The aqueous phase was washed with chloroform (3×), and the combined organic extracts were concentrated to an oil which was taken up in 5% aqueous sodium bicarbonate and extracted with chloroform (3×). The combined organic extracts of the acidified aqueous phase were dried (magnesium sulfate) and then concentrated to give an oil, which was purified by chromatography (acid-washed silica gel, 10:1 chloroform/acetonitrile) to give 5-[(5-Bromo-1-naphthalenyl)sulfonyl]-2,4-thiazolidinedione (7.6 g, 42% yield): mp 189°–190° C. (acetonitrile/chloroform): $^1$H NMR (DMSO-$d_6$, 200 MHz) δ 6.60 (s, 1 H, CH, exchanges with $D_2O$), 7,7–8.7 (m, 6 H, ArH).

Method B. 5-[(1-Bromo-2-naphthalenyl)thio]-2,4-thiazolidinedione. A solution of 5-bromo-2,4-thiazolidinedione (2.54 g, 13 mmol) and 1-bromo-2-mercaptonaphthalene (2.91 g, 13 mmol) in THF (100 mL) under nitrogen at $-78°$ C. was treated with lithium diisopropylamide (14.7 mL, 28.6 mmol, 1.94M in THF). After 30 minutes, the mixture was allowed to warm to $25°$ C. After 1 hour, 2N aqueous hydrochloric acid was added. The aqueous phase was extracted with ethyl acetate (3×), and the combined organic extracts were dried (magnesium sulfate) and concentrated to give a yellow oil (5.27 g). Chromatography of this material (acid-washed silica gel, chloroform) gave 5-[(1-Bromo-2-naphthalenyl)thio]-2,4-thiazolidinedione (3.68 g, 83% yield): mp 128°–129° C. (hexane/ethyl acetate); $^1$H NMR (DMSO-$d_6$, 400 MHz) δ 6.42 (s, 1 H, CH), 7.6–8.2 (m, 6 H, ArH).

Method C. 5-(2-Naphthalenylsulfonyl)-2,4-thiazolidinedione. To a solution of 5-(2-thianaphthalenyl)-2,4-thiazolidinedion (2.5 g, 9.1 mmol) in acetic acid (100 mL) at $60°$ C. was added 30% aqueous hydrogen peroxide (10 mL, 88 mmol). This was followed by two equivalent additions of hydrogen peroxide at reaction times of 30 and 90 minutes. At 3 hours, the reaction mixture was poured into water (600 mL) and the aqueous phase extracted with ethyl acetate (3×). The combined organic extracts were dried (magnesium sulfate) and concentrated to give an oil which was purified by chromatography (C-18 silica gel, 70:30 methanol/water) to give 2 as a foam (1.7 g, 62% yield). Crystallization from hexane/chloroform/methanol gave white needles of 5-(2-Naphthalenylsulfonyl)-2,4-thiazolidinedione (1.31 g, 47% yield): mp 196°–197° C.; $^1$H NMR (DMSO-$d_6$, 400 MHz) δ 6.75 (s, 1 H CH, exchanges with $D_2O$) 7.7–8.6 (m, 7 H, ArH).

5-Bromo-2,4-thiazolidinedione. To a solution of 2,4-thiazolidinedione (100 g, 0.885 mol) in acetic acid (250 mL) at 85° C. was added bromine (42.7 mL, 0.885 mol) dropwise over 1 hour. After an additional 1 hour at 85° C., the solution was allowed to cool to ambient temperature and then poured into water (1 L). The crude product was extracted into ether, dried (magnesium sulfate), and concentrated to give a yellow oil (127 g) which was filtered through a short column of silica gel (8:1 chloroform/acetonitrile). The resulting oil was triturated with hexane to give 5-Bromo-2,4-thiazolidinedione as a white powder (95.0 g, 57% yield): mp 61°–62° C.; $^1$H NMR (acetone-$d_6$, 200 MHz) δ 6.41 (s, 1 H, CH), 11.30 (s, 1 H, NH).

5-(2-Naphthalenyloxy)-2,4-thiazolidinedione. By a procedure similar to that of method B, a solution of 2-naphthol (5.0 g, 35 mmol) and 5-bromo-2,4-thiazolidinedione (6.8 g, 35 mmol) in THF (200 mL) was treated with lithium bis(tri-methylsilyl)amide (76 mL, 76 mmol, 1.0M in THF) to give, after chromatography (acid-washed silica gel, chloroform/acetonitrile), 5-(2-Naphthalenyloxy)-2,4-thiazolidinedione (2.8 g, 31% yield): mp 221°–222° C. (acetone/ethyl acetate); $^1$H NMR (DMSO-$d_6$, 400 MHz) δ 6.52 (s, 1 H, OCH), 7.1–8.0 (m, 6 H, ArH), 10.57 (s, 1 H, ArH).

5-(2-Naphthalenylsulfinyl)-2,4-thiazolidinedione. To a solution of 5-(2-thianaphthalenyl)-2,4-thiazolidinedione (1.0 g, 3.6 mmol) in dichloromethane (100 mL) was added m-chloroperbenzoic acid (0.74 g, 85%, 3.6 mmol) portionwise over 30 minutes. After an additional 30 minutes, dimethyl sulfide (0.5 mL) was added and the solution concentrated. The resulting solid was washed repeatedly with hot carbon tetrachloride to remove m-chlorobenzoic acid. Recrystallization of the remaining solid (1.1 g) gave 5-(2-Naphthalenylsulfinyl)-2,4-thiazolidinedione as a 3:1 mixture of diastereomers (0.55 g, 52% yield): mp 157°–158° C. (acetonitrile/carbon tetrachloride); $^1$H NMR (DMSO-$d_6$, 400 MHz) δ 6.31 (s, 0.75 H, CH), 6.49 (s, 0.25 H, CH), 7.61–8.19 (m, 6 H, ArH), 8.25 (s, 0.25 H, ArH), 8.31 (s, 0.75 H, ArH). HPLC analysis ($C_{18}$ silica gel, 30% acetonitrile/70% 0.01M aqueous $NH_4H_2PO_4$, 1.5 mL/min) of the diastereomeric mixture gave two peaks which tailed into each other, indicating an on column interconversion ($t_R$=5.71 minutes (major isomer); $t_R$=3.86 minutes (minor isomer)). Reinjection of the material corresponding to each peak reproduced the original HPLC trace.

5-[[4-[(1-Methylcyclohexyl)methoxy]phenyl]sulfonyl]-2,4-thiazolidinedione. Sodium hydride (3.17 g, 66.1 mmol, 50% in oil) was added to a solution of (1-methylcyclohexl) methanol (8.47 g, 66.1 mmol) in dimethylformamide (30 mL). The mixture was heated to 55° C. for 30 minutes. A solution of 5-[(4-fluorophenyl)sulfonyl]-2,4-thiazolidinedione (1.82 g, 6.61 mmol) in dimethylformamide (20 mL) was then added. After 3 hours at 55° C., the reaction mixture was poured into 2N aqueous hydrochloric acid. The aqueous phase was extracted with ethyl acetate (3×). The organic extracts were dried (magnesium sulfate) and then concentrated to an oil which was purified by chromatography (C-18 silica gel, 70:30 methanol/water). The resulting white foam (1.31 g) was rechromatographed (acid-washed silica gel, chloroform) and then recrystallized from hexane/ethyl acetate/ether to give 5-[[4-[(1-Methylcyclohexyl)methoxy]phenyl]sulfonyl]-2,4-thiazolidinedione as a white powder (0.97 g, 38% yield) mp 174°–175° C.; $^1$H NMR (DMSO-$d_6$, 400 MHz) δ 1.00 (s, 3 H, $CH_3$), 1.20–1.60 (m, 10 H, cyclohexyl $CH_2$'s), 3.82 (s, 2 H, $OCH_2$). 6.56 (s, 1 H, CH), 7.22 (d, J=9 Hz, 2 H, ArH), 7.80 (d, J=9 Hz, 2 H, ArH).

5-[(5-Bromo-1-naphthalenyl)sulfonyl]-3-methyl-2,4-thiazolidinedione. To a solution of 5-[(Bromo-1-naphthalenyl)sulfonyl]-2,4-thiazolidinedione (2.0 g, 5.2 mmol) in THF/dimethylformamide (1:1 40 mL) at 25° C. under nitrogen was added sodium hydride (0.25 g, 5.2 mmol, 50% in oil). After 30 minutes, iodomethane (0.32 mL, 5.2 mmol) was added. The reaction was stirred for 1 hour and then partitioned between 5% aqueous sulfuric acid and chloroform. The organic phase was dried (magnesium sulfate) and concentrated to give crude product. Chromatography (silica gel, chloroform) and recrystallization (2× chloroform/ether) gave 5-[(5-Bromo-1-naphthalenyl)sulfonyl]-3-methyl-2,4-thiazolidinedione (520 mg, 25% yield): mp 150°–151° C. $^1$H NMR (CDCl$_3$, 400 MHz) δ 3.03 (s, 3 H, $CH_3$), 5.59 (s, 1 H, CH) 7.6–8.8 (m, 6 H, ArH).

5-[(5-Bromo-1-naphthalenyl)sulfonyl]-3,5-dimethyl-2,4-thiazolidinedione. To a solution of 5-[(Bromo-1-naphthalenyl)sulfonyl]-2,4-thiazolidinedione (1.1 g, 2.9 mmol) in acetone (50 mL) at 25° C. was added anhydrous potassium carbonate (3.9 g, 29 mmol) and iodomethane (1.8 mL, 29 mmol). After 1 hour, the mixture was filtered and the filtrate concentrated. Purification by chromatography (acid-washed silica gel, carboetetrachloride/chloroform) followed by recrystallization (chloroform/hexane/exane) gave 5-[(5-Bromo-1-naphthalenyl)sulfonyl]-3,5-dimethyl-2,4-thiazolidinedione (0.69 g, 59% yield): mp 160°–161° C. $^1$H NMR (CDCl$_3$, 400 MHz) δ 2.10 (s, 3 H, $CH_3$), 2.69 (s, 3 H, $NCH_3$) 7.5–8.9 (m, 6 H, ArH).

5-[(6-Hydroxyl-2-naphthalenyl)thio]-2,4-thiazolidinedione. Potassium hydroxide (2.47 g, 44.0 mmol) was added to a suspension of 5-[(6-ethoxycarbonyloxy-2-naphthalenyl)thio]-2,4-thiazolidinedione (8.0 g, 22 mmol) in methanol (50 mL) at 25° C. After 30 minutes, the resulting solution was acidified to pH=1 with and then extracted with ethyl acetate (3×). The combined extracts were dried (magnesium sulfate) and concentrated to give 5-[(6-Hydroxyl-2-naphthalenyl)thio]-2,4-thiazolidinedione as a powder (6.4 g, 99% yield): mp 182°–183° C. (chloroform/ ethyl acetate); $^1$H NMR (DMSO-$d_6$, 400 MHz) δ 6.07 (s, 1 H CH). 7.1–8.0 (m, 6 H, ArH). Analogue 35 was prepared similarly, with the use of 3 molar equivalents of potassium hydroxide.

3. Administration of Therapeutic Compounds

A. Formulations

Using a method of the invention, therapeutic compounds are typically administered to human patients topically. Oral and parenteral administration are used in appropriate circumstances apparent to the practitioner. Preferably, the compositions are administered in unit dosage forms suitable for single administration of precise dosage amounts.

To prepare a topical formulation, a therapeutically effective concentration of the compound is placed in a dermatological vehicle as is known in the art. The amount of the therapeutic compound to be administered and the compound's concentration in the topical formulations depend upon the vehicle selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

The concentration of the therapeutic compound for topical formulations is in the range of about 1 mg/ml to about 100 mg/ml. Typically, the concentration of the therapeutic compound for topical formulations is in the range of about 2.5 mg/ml to about 25 mg/ml. Solid dispersions of the therapeutic compound as well as solubilized preparations can be used. Thus, the precise concentration is subject to modest experimental manipulation in order to optimize the therapeutic response. About 2,500 mg of therapeutic compound per 100 grams of vehicle is useful in the treatment of skin lesions to provide a 2.5% weight/weight (w/w) formulation. Suitable vehicles include oil-in-water or water-in-oil emulsions using mineral oils, petrolatum and the like as well as gels such as hydrogel.

Alternative topical formulations include shampoo preparations, oral paste, and mouth wash preparations. ORABASE® can be used as the base oral paste to which the therapeutic compound is added. Concentrations of therapeutic compound are typically as stated above for topical formulations.

The therapeutic compound is optionally administered topically by the use of a transdermal therapeutic system (see Barry, *Dermatological Formulations,* (1983) p. 181 and literature cited therein). While such topical delivery systems have been designed largely for transdermal administration of low molecular weight drugs, by definition they are capable of percutaneous delivery. They may be readily adapted to administration of the therapeutic compounds of the invention by appropriate selection of the rate-controlling microporous membrane.

For ophthalmic applications, such as treatment of keratitis, the therapeutic compound is formulated into solutions, suspensions, and ointments appropriate for use in the eye. The concentrations are usually as discussed above for topical preparations. For ophthalmic formulations, see Mitra (ed.), *Ophthalmic Drug Delivery Systems,* Marcel Dekker, Inc., New York, N.Y. (1993) and also Havener, W. H., *Ocular Pharmacology,* C. V. Mosby Co., St. Louis (1983).

The therapeutic compound is alternatively administered by aerosol. This is accomplished by preparing an aqueous aerosol, liposomal preparation or solid particles containing the compound. A nonaqueous (e.g., fluorocarbon propellent) suspension could be used. Sonic nebulizers are preferred because they minimize exposing the therapeutic compound to shear, which can result in degradation of the compound.

Ordinarily, an aqueous aerosol is made by formulating an aqueous solution or suspension of the therapeutic compound together with conventional pharmaceutically acceptable carriers and stabilizers. The carriers and stabilizers vary with the requirements of the particular compound, but typically include nonionic is surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

For oral administration, either solid or fluid unit dosage forms can be prepared. For preparing solid compositions such as tablets, thiazolidine derivatives are mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the thiazolidine compound with an inert pharmaceutical diluent and filling the mixture into a hard gelatin capsule of appropriate size. Soft gelatin capsules are prepared by machine encapsulation of a slurry of the thiazolidine compound with an acceptable vegetable oil, light liquid petrolatum or other inert oil.

Fluid unit dosage forms for oral administration such as syrups, elixirs and suspensions can be prepared. The water-soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill. Usually, the therapeutic compound is prepared in an aqueous solution (discussed below) in a concentration of from about 1 to about 100 mg/ml. More typically, the concentration is from about 10 to about 20 mg/ml. The formulation, which is sterile, is suitable for various parenteral routes including intra-dermal, intra-articular, intra-muscular, intravascular, and subcutaneous.

In addition to the therapeutic compound, the compositions may include, depending on the formulation desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline solutions, Ringer's solution, dextrose solution, and Hank's solution. In addition, the pharmaceutical composition or formulation may include additives such as other carriers; adjuvants; or nontoxic, nontherapeutic, nonimmunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives and excipients are those amounts which are effective to obtain a pharmaceutically acceptable formulation in terms of solubility, biological activity, etc.

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals.

Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described.

Thus, a composition of the invention includes a therapeutic compound which may be formulated with conventional, pharmaceutically acceptable, vehicles for topical, oral or parenteral administration. Formulations may also include small amounts of adjuvants such as buffers and preservatives to maintain isotonicity, physiological and pH stability. Means of preparation, formulation and administration are known to those of skill. See generally *Remington's Pharmaceutical Science* 15th ed., Mack Publishing Co., Easton, Pa. (1980).

B. Slow Release Delivery

Slow or extended-release delivery systems, including any of a number of biopolymers (biological-based systems), systems employing liposomes, and polymeric delivery systems, can be utilized with the compositions described herein to provide a continuous or longterm source of therapeutic compound. Such slow release systems are applicable to formulations for topical, ophthalmic, oral, and parenteral use.

C. Routes of Administration

Therapeutic agents of the invention are usually delivered or administered topically or by transdermal patches for treating dermal psoriasis. Alternatively, oral administration is used. Additionally, the agents can be delivered parenterally, especially for treatment of arthritis, such as psoriatic arthritis, and for direct injection of skin lesions. Parenteral therapy is typically intra-dermal, intra-articular, intramuscular or intravenous.

A preferred way to practice the invention is to apply the thiazolidinedione compound, in a cream or oil based carrier, directly to the psoriatic lesions. Typically, the concentration of therapeutic compopund in a cream or oil is 1–2%. Alternatively, an aerosol can be used topically. These compounds can also be orally administered. The thiazolidinedione compound trogitazone (Sankyo's CS-045 and Parke-Davis' CI-991), is an example of a thiazolidinedione that can be used in this fashion.

In general, the route of administration is topical (including administration to the eye, scalp, and mucous membranes), oral, or parenteral. Topical administration is preferred in treatment of skin lesions, including lesions of the scalp, lesions of the cornea (keratitis), and lesions of mucous membranes where such direct application is practical. Shampoo formulations are sometimes advantageous for treating scalp lesions such as seborrheic dermatitis and psoriasis of the scalp. Mouthwash and oral paste formulations can be advantageous for mucous membrane lesions, such as oral lesions and leukoplakia. Oral administration is a preferred alternative for treatment of skin lesions and other lesions discussed above where direct topical application is not as practical, and it is a preferred route for other applications.

Intra-articular injection is a preferred alternative in the case of treating one or only a few (such as 2–6) joints. Usually, the compound is delivered in an aqueous solution of about 10–20 mg/ml. Additionally, the therapeutic compounds are injected directly into lesions (intra-lesion administration) in appropriate cases. Intra-dermal administration is an alternative for dermal lesions such as those of psoriasis.

D. Dosages and Schedules

An effective quantity of thiazolidine derivative is employed in treatment. The dosage of compounds used in accordance with the invention varies depending on the compound and the condition being treated. The age, weight, and clinical condition of the recipient patient; and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

Broadly, a dosing schedule is from about 100 to about 600 mg twice a day. More typically, a single dose is about 100–200 mg of compound given twice a day. A convenient oral dose for an adult patient is 200 mg twice a day. A dosage range for topical treatment is about 0.1% to about 10% (weight/volume) in a cream, applied twice a day. A usual dose for intra-articular injection is 20–40 mg injected per joint, not generally exceeding three joints per therapy session. A typical dosage for intra-dermal administration is about 20–75 mg per injection per site.

Typically, the dosage is administered at least once a day until a therapeutic result is achieved. Preferably, the dosage is administered twice a day, but more or less frequent dosing can be recommended by the clinician. Once a therapeutic result is achieved, the drug can be tapered or discontinued. Occasionally, side effects warrant discontinuation of therapy. In general, an effective amount of the compound is that which provides either subjective relief of symptoms or an objectively identifiable improvement as noted by the clinician or other qualified observer.

The foregoing is offered primarily for purposes of illustration. It will be readily apparent to those of ordinary skill in the art that the operating conditions, materials, procedural steps and other parameters of the system described herein may be further modified or substituted in various ways without departing from the spirit and scope of the invention. For example, the invention has been described with human patients as the usual recipient, but veterinary use is also contemplated. Thus, the invention is not limited by the preceding description, but rather by the appended claims. All cited literature is incorporated by reference.

EXAMPLES

Example 1

Effect of Ciglitazone on Growth of Cultured Adult Human Keratinocytes

Adult human keratinocytes, obtained by keratome biopsy, were cultured in low calcium, serum free media (MCDB, see Boyce, B. A. and R. G. Ham, *J. Investigative Derm.* 81 (1) 335–405 (July 1983)) in the presence of each of the following: vehicle (0.1% dimethyl sulfoxide (DMSO)), 0.1 $\mu$M, 1.0 $\mu$M, 2.0 $\mu$M, 5.0 $\mu$M, and 10 $\mu$M ciglitazone for 4 days. Cell number was assessed at time zero (before treatment) and at the end of the treatment period by the neutral red dye assay. See Kitano, et al., *Euro. J. Clin. Investg.* 21: 53–58 (1991) and West, et al., *J. Investigative Derm.* 99 (1) 95–100 (1992). Each condition was performed in 12 replicates, on keratinocytes from two individuals identified as sample A and sample B in the figures. Data displayed are means ± standard errors.

The use of proliferating human keratinocytes in culture as a test system for determining the utility of a compound for treating psoriasis is well documented. For example, vitamin D (1,25-dihydroxyvitamin D) compounds and retinoid compounds show antiproliferative effects against keratinocytes in culture and are useful agents for treating psoriasis (Kitano et al., West et al.).

Figure 2:
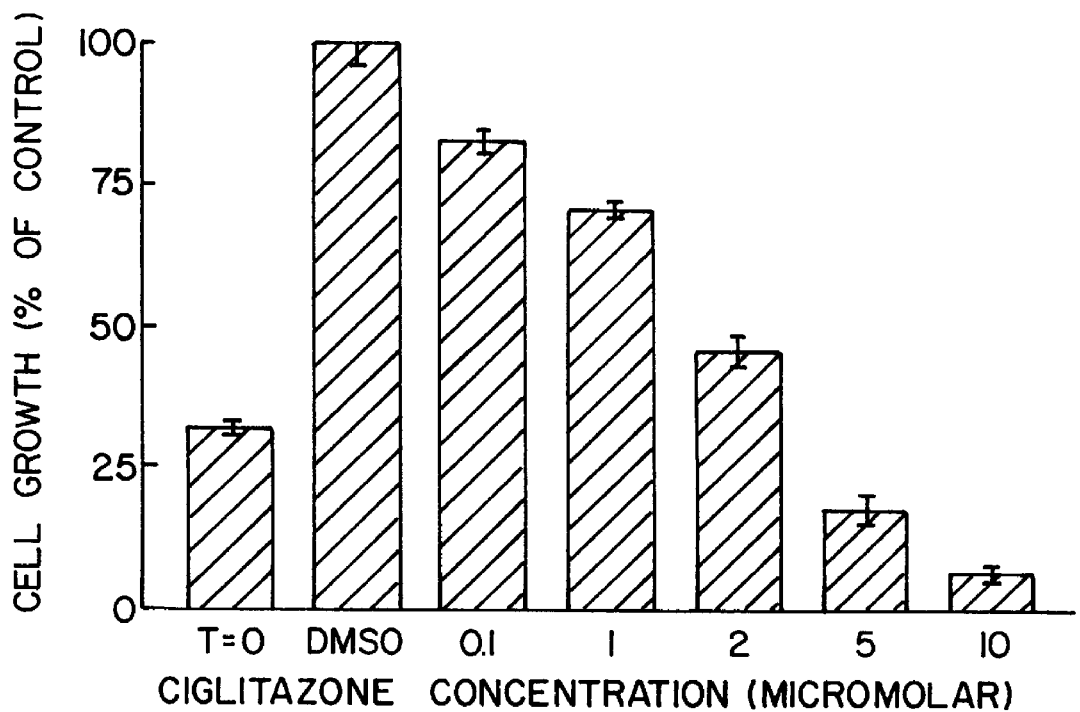
FIG. 2 shows a dose response graph of the application of ciglitazone to keratinocytes taken from an adult human, subject B, and grown in cell culture.
Figure 3:
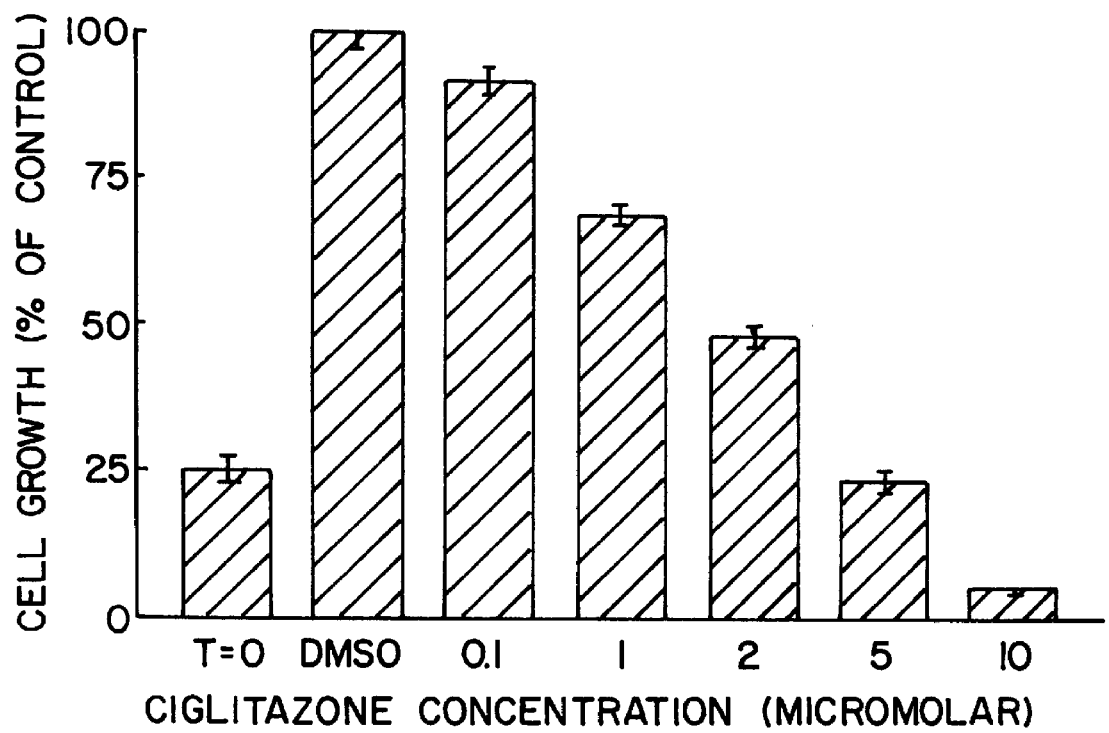
FIG. 3 shows a dose response graph of the application of ciglitazone to keratinocytes as a mean of the data displayed in FIG. 1 and FIG. 2.
Figure 4:
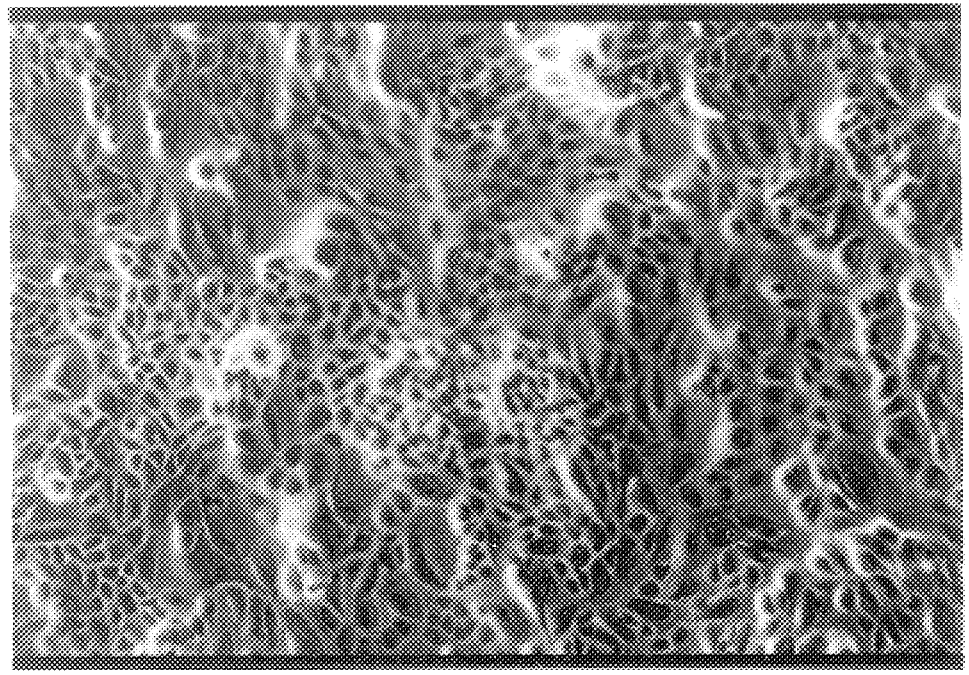
FIG. 4 is a photomicrograph of keratinocytes obtained by keratome biopsy from subject A and maintained in culture without any ciglitazone.
Figure 5:
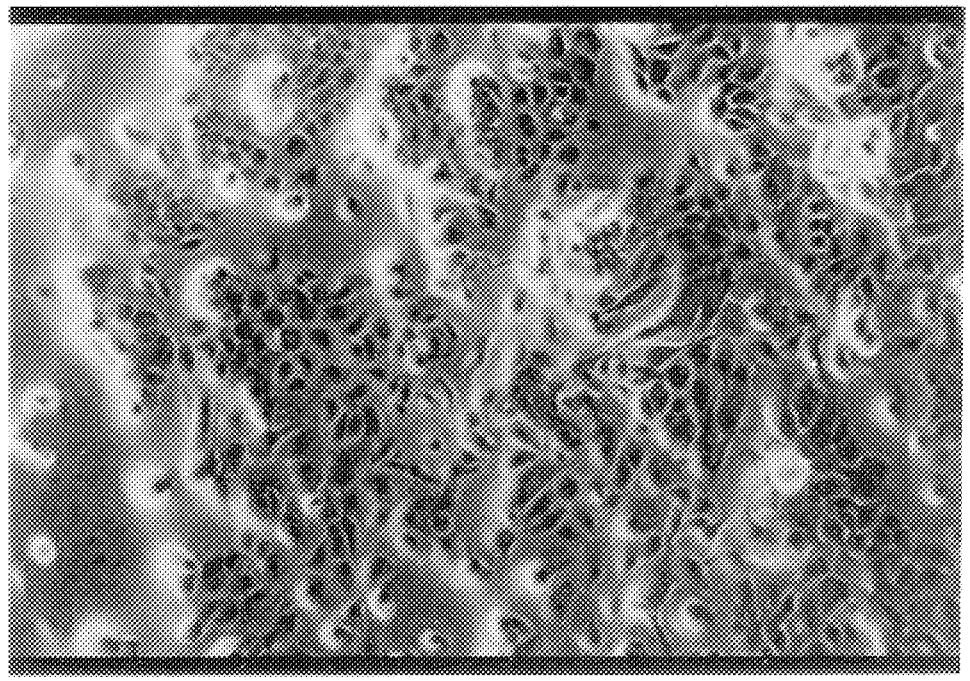
FIG. 5 is a photomicrograph of cultured keratinocytes from subject A exposed to 0.1 micromolar ciglitazone.
Figure 6:
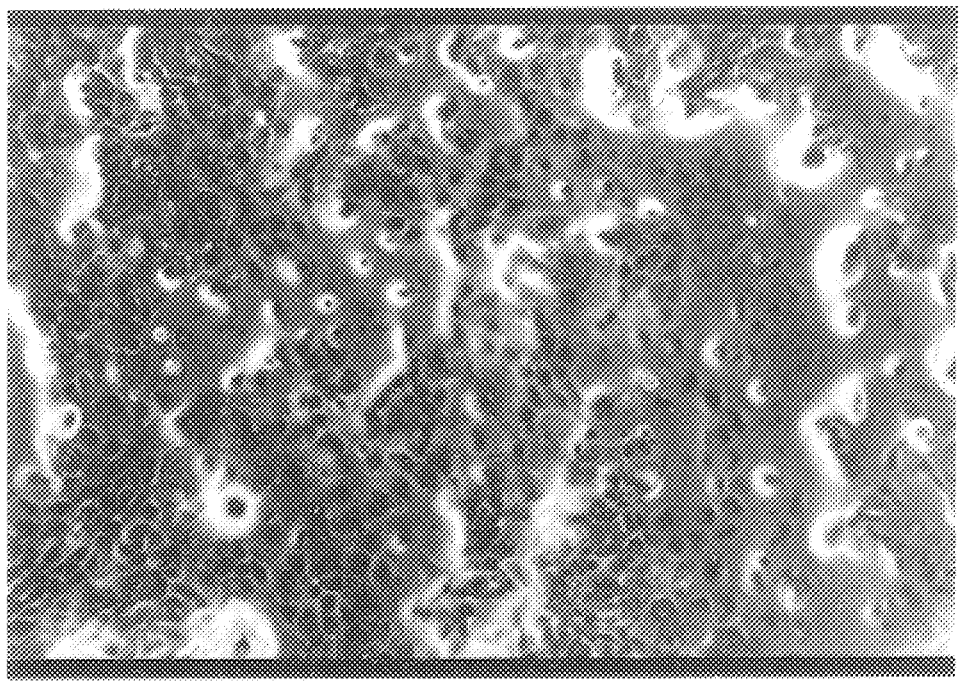
FIG. 6 is a photomicrograph of cultured keratinocytes from subject A exposed to 1 micromolar ciglitazone.
Figure 7:
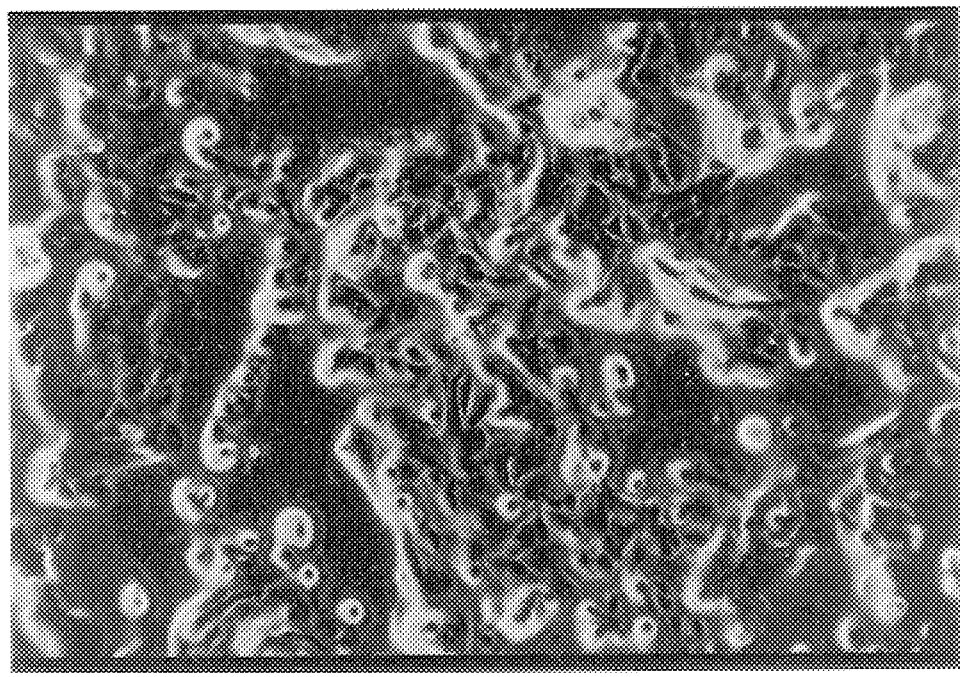
FIG. 7 is a photomicrograph of cultured keratinocytes from subject A exposed to 2 micromolar ciglitazone.
Figure 8:
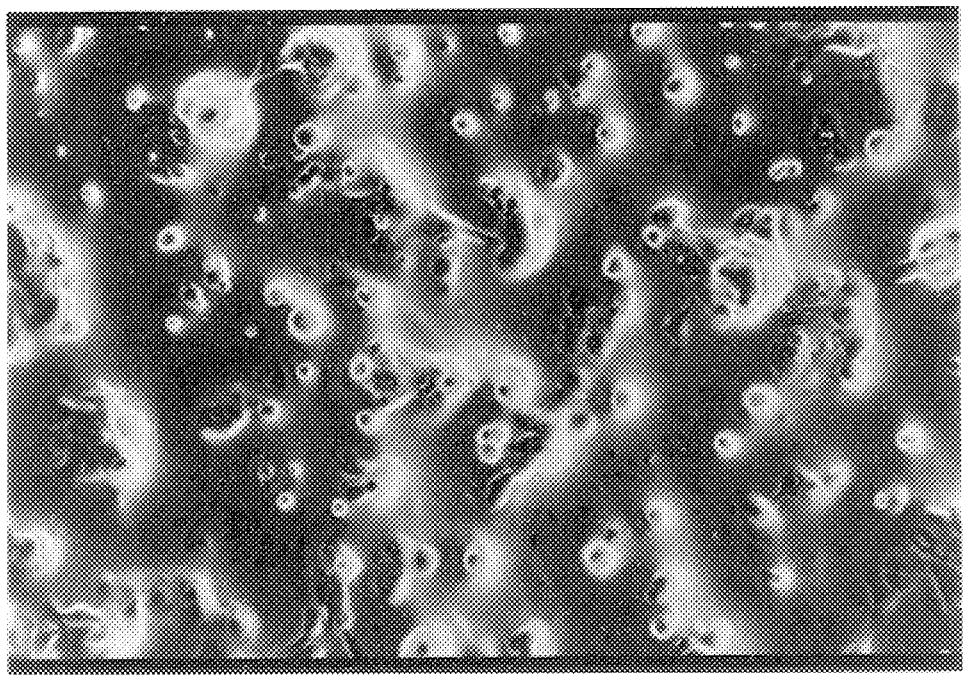
FIG. 8 is a photomicrograph of cultured keratinocytes from subject A exposed to 5 micromolar ciglitazone.
Figure 9:
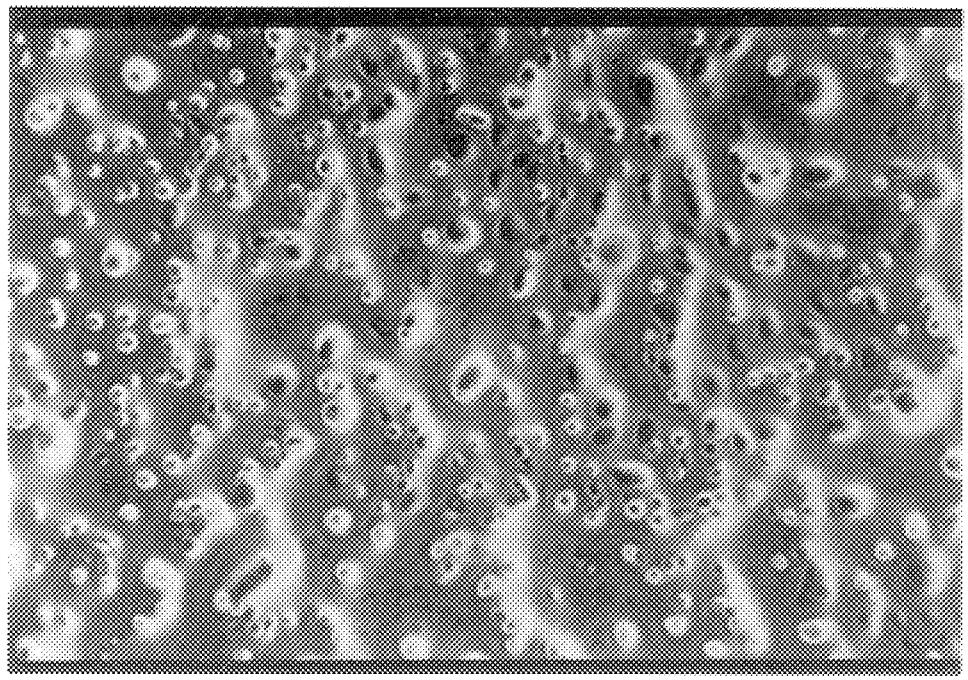
FIG. 9 is a photomicrograph of cultured keratinocytes from subject A exposed to 10 micromolar ciglitazone.
Figure 10:
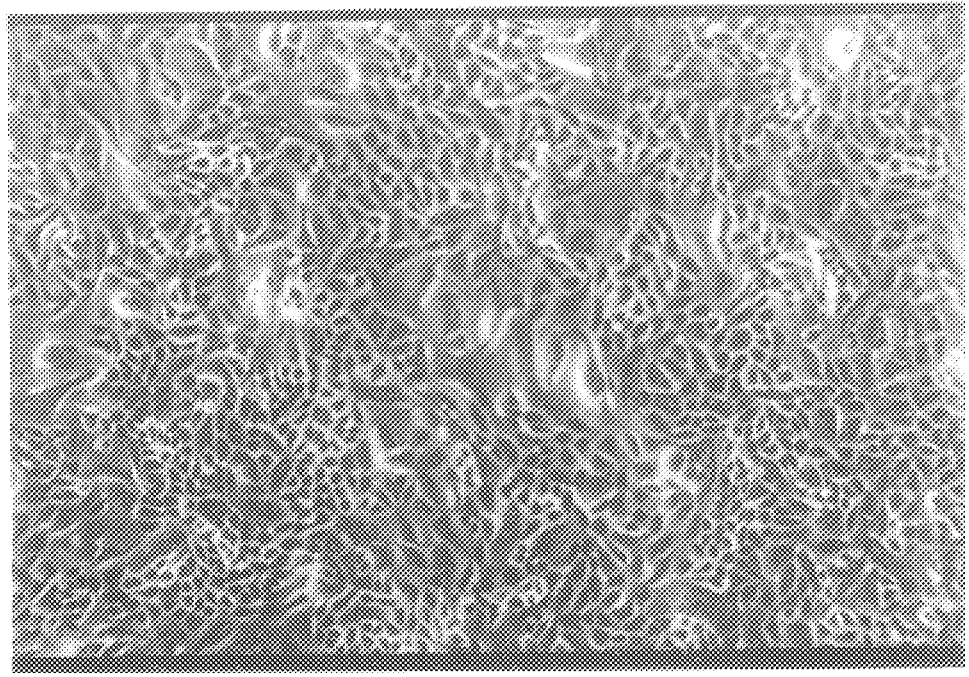
FIG. 10 is a photomicrograph of keratinocytes obtained by keratome biopsy from subject B and maintained in culture without any ciglitazone.
Figure 11:
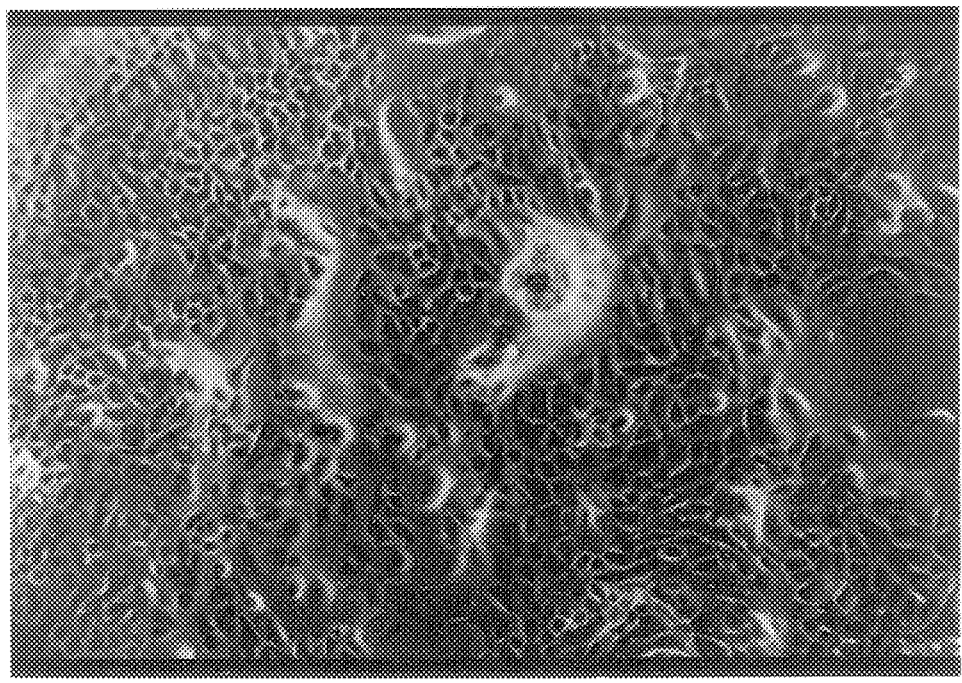
FIG. 11 is a photomicrograph of cultured keratinocytes from subject B exposed to 0.1 micromolar ciglitazone.
Figure 12:
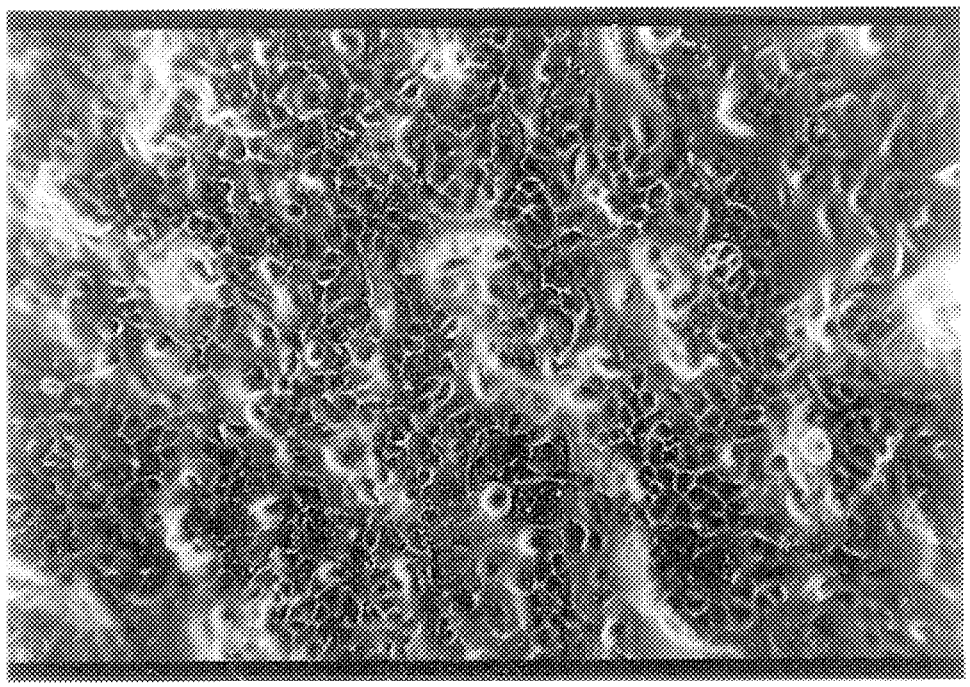
FIG. 12 is a photomicrograph of cultured keratinocytes from subject B exposed to 1 micromolar ciglitazone.
Figure 13:
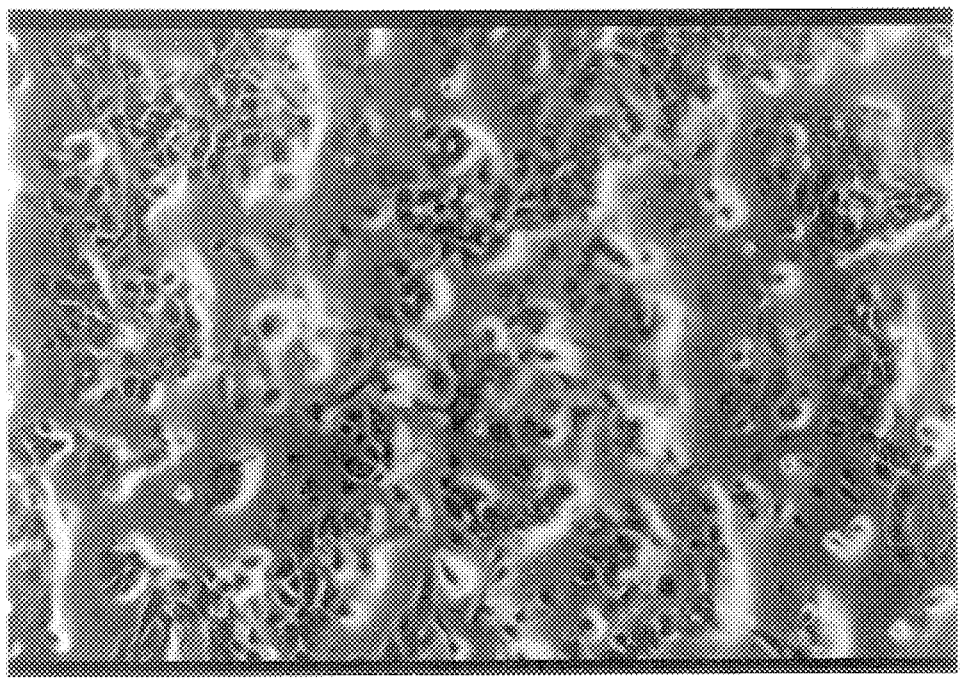
FIG. 13 is a photomicrograph of cultured keratinocytes from subject B exposed to 2 micromolar ciglitazone.
Figure 14:
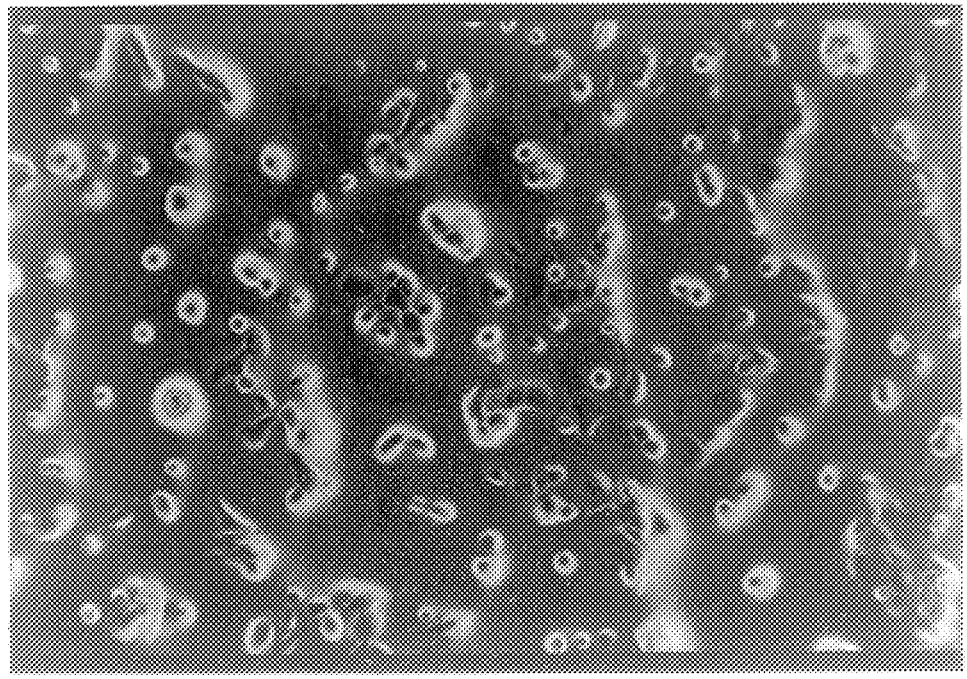
FIG. 14 is a photomicrograph of cultured keratinocytes from subject B exposed to 5 micromolar ciglitazone.
Figure 15:
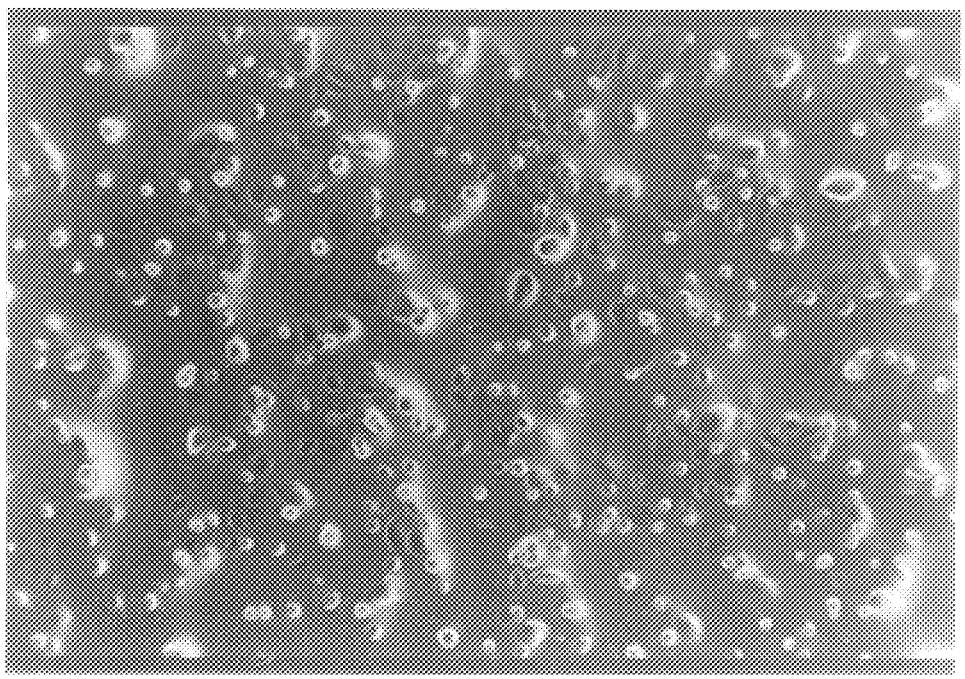
FIG. 15 is a photomicrograph of cultured keratinocytes from subject B exposed to 10 micromolar ciglitazone.

The data are presented in graphic form in FIGS. 1–3. FIG. 1 displays the results of sample A taken from a first individual. The coordinate plots the cell growth of the keratinocytes as the percentage of controls. The ordinate plots the micromolar concentration of the therapeutic compound, ciglitazone. FIG. 2 uses equivalent parameters except that sample B was taken from a second individual. FIG. 3 is a composite showing the mean of the combination of data from samples A and B.

Photomicrographs of keratinocytes, under each treatment condition, were taken at the end of the treatment period. See FIGS. 4–15. FIGS. 4–9 are photomicrographs of cultured keratinocytes from an adult human, subject A, after exposure to various concentrations of ciglitazone. The drug concentrations were 0, 0.1, 1, 2, 5, and 10 micromolar. FIGS. 10–15 are photomicrographs of cultured keratinocytes from an adult human, subject B, after exposure to the same concentrations of ciglitazone as above. The photomicrographs from both subjects A and B show decreased cellular profileration with increasing doses of drug.

As demonstrated by the data, application of ciglitazone to keratinocytes taken from human adults results in a dose response inhibition of cell growth. Specifically, the normal proliferation of the skin cells in culture was inhibited in a dose dependent fashion by the application of ciglitazone.

Example 2

A Clinical Trial, Topical Therapy

A patient having dermal manifestations of psoriasis is selected for therapy using the invention. Ciglitazone in a cream vehicle and having a concentration of 2% (weight/volume) is applied to the affected skin three times a day. After the skin lesions have subsided, therapy is discontinued.

Example 3

A Clinical Trial, Oral Therapy

A patient having psoriasis afflicting multiple areas of the skin as well as the nails and scalp is selected for therapy. The patient weighs 80 kilograms and, other than the psoriasis, enjoys good health. Ciglitazone in a dosage of 200 milligrams is administered twice a day. The patient is monitored for improvement in his manifestations of psoriasis as well as for any changes in his blood pressure and blood glucose concentration. Additionally, a complete blood count, including white cell count and differential, a platelet count, and liver function tests (such as levels of alkaline phosphatase, lactose dehydrogenase, and transaminases) are checked prior to treatment and periodically thereafter. The dosage is tapered and discontinued when the manifestations of psoriasis subside.

Example 4

A Clinical Trial, Topical and Intra-articular Administration

A patient having psoriasis with involvement of the skin and several of the small joints of the hand is selected for therapy. The patient is treated with topical application of ciglitazone as described in Example 2. Additionally, the patient is treated with intra-articular injections of ciglitazone directly into the afflicted small joints of the hand. An aqueous solution of concentration 10 mg/ml is used. Each joint is injected with 20–40 mg of ciglitazone, not exceeding three joints per therapy session. The injection directly into the joints is repeated weekly until a suitable response is experienced.

Example 5

A Clinical Trial, Intra-dermal Administration

A patient having psoriasis is treated with intra-dermal injection of ciglitazone in a 20 mg/ml aqueous solution. About 20–75 mg are injected directly into each site or dermal lesion treated. The therapy is repeated weekly until the injected lesions diminish or vanish.

What is claimed is:

1. A method for treating acne vulgaris in a human in need thereof by administration of an effective amount of a 5-aryl substituted thiazolidine derivative of formula I

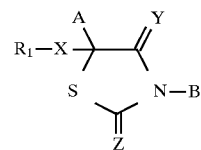

where:
  $R_1$ is an unsaturated carbocyclic or an unsaturated heterocyclic;
  A is H or methyl;
  B is H or methyl;
  X is a lower alkylene or a bond; or —HC=CH—; or O, $CH_2$, $CH_2S$, $CH_2SO_2$, S, SO, or $SO_2$;
  Y is oxo or imino;
  Z is oxo or imino;
  and pharmaceutically acceptable salts thereof with the proviso that if X is $H_2C=$ and Y is imino, then $R_1$ is not of the formula

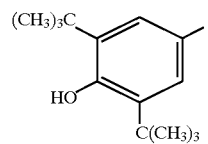

2. A method of claim 1 wherein the thiazolidine derivative is a thiazolidine-dione having both Y and Z as oxo.

3. A method of claim 1 wherein the thiazolidine derivative is further selected from compounds where $R_1$ is a substituted benzyl and X is a lower alkylene radical.

4. A method of claim 3 wherein the thiazolidine derivative is selected from compounds wherein $R_1$ is of the formula IIa

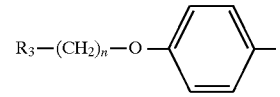

where n is an integer from 1 to 4, and where $R_3$ is of the formula IIb

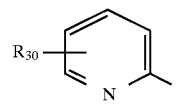

where $R_{30}$ is a lower alkyl of 1–4 carbons; or $R_3$ is of the formula IIc

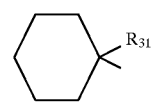

where $R_{31}$ is hydrogen or a lower alkyl of 1–4 carbons and the cyclohexane ring may be optionally substituted at any available methylene with single oxo or hydroxy; or, where $R_3$ is of the formula IId

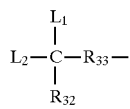

wherein $R_{32}$ is alkyl, cycloalkyl, phenylalkyl, phenyl, a five- or six-membered heterocyclic group including one or two hetero-atoms selected from the group consisting of nitrogen, oxygen and sulfur, or a group of the formula IIe

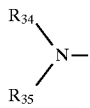

where $R_{34}$ and $R_{35}$ are the same or different and each is lower alkyl or $R_{34}$ and $R_{35}$ are combined to each other either directly or as interrupted by a hetero-atom selected from the group consisting of nitrogen, oxygen and sulfur to form a five- or six-membered ring as taken together with the nitrogen atom adjacent to $R_{34}$ and $R_{35}$; $R_{33}$ is a bond or a lower alkylene group, $L_1$ and $L_2$ may be the same or different and each is a lower alkyl or $L_1$ and $L_2$ are combined to each other to form an alkylene group, provided that when $R_{32}$ is other than alkyl, $L_1$ and $L_2$ may further be hydrogen.

5. A method of claim 4 wherein Y and Z are both oxo and n is 1 or 2.

6. A method of claim 1 wherein the thiazolidine derivative is further selected from compounds where X is methylene; and $R_1$ is of formula IV

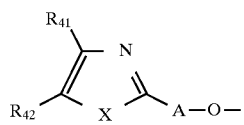

wherein X is an oxygen or sulfur atom, $R_{41}$ and $R_{42}$ are each independently hydrogen or a hydrocarbon residue which may optionally be substituted and $R_{41}$ and $R_{42}$ may jointly, together with the oxazole or thiazole ring, form a condensed ring and A is a lower alkylene group.

7. A method of claim 1 wherein the thiazolidine derivative is further selected from compounds where X is methylene or —HC═CH— and $R_1$ is of formula V

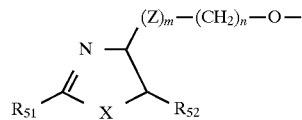

wherein
$R_{51}$ is hydrogen or a hydrocarbon residue or heterocyclic residue which may each be substituted;
$R_{52}$ is hydrogen or a lower alkyl group which may be substituted by hydroxyl group;
X is an oxygen or sulfur atom;
Z is a hydroxylated methylene or carbonyl;
m is 0 or 1;
n is an integer of 1 to 3;
and pharmaceutically acceptable salts thereof.

8. A method of claim 1 wherein the thiazolidine derivative is further selected from compounds where X is methylene and $R_1$ is of formula VI

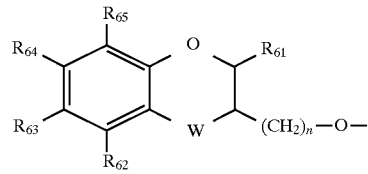

wherein $R_{61}$ and $R_{62}$ are the same or different and each represents a hydrogen atom or a ($C_1$–$C_5$) alkyl group;

$R_{63}$ represents a hydrogen atom, a ($C_1$–$C_6$) aliphatic acyl group, an alicyclic acyl group, an aromatic acyl group, a heterocyclic acyl group, an araliphatic acyl group, a ($C_1$–$C_6$ alkoxy) carbonyl group or an aralkyloxycarbonyl group;

$R_{64}$ and $R_{65}$ are the same or different and each represents a hydrogen atom, a ($C_1$–$C_5$) alkyl group or a ($C_1$–$C_5$) alkoxy group, or $R_{64}$ and $R_{65}$ together represent a ($C_1$–$C_4$) alkylenedioxy group;

W represents the —$CH_2$—, >CO or >CH—O—$R_{66}$ group (in which $R_{66}$ represents any one of the atoms or groups defined for $R_{63}$ and may be the same as or different from $R_{63}$, and where n is an integer from 1 to 10.

9. A method of claim 1 wherein the thiazolidine derivative is further selected from compounds where X is a methylene and $R_1$ is of formula VII

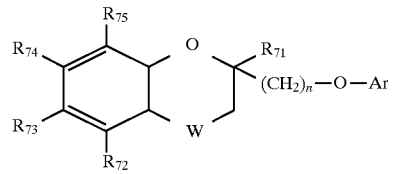

wherein:

$R_{71}$ represents a hydrogen atom, a ($C_1$–$C_{25}$) alkyl group, a ($C_3$–$C_{10}$) cycloalkyl group or a substituted ($C_3$–$C_{10}$) cycloalkyl group having at least one ($C_1$–$C_6$) alkyl substituent;

$R_{72}$, $R_{74}$ and $R_{75}$ are the same or different and each represents: a hydrogen atom; a ($C_1$–$C_{25}$) alkyl group; a substituted ($C_1$–$C_{26}$) having at least one of substituents (a); an aralkyl group; a ($C_3$–$C_{10}$) cycloalkyl group; a substituted ($C_3$–$C_{10}$) cycloalkyl group having at least one ($C_1$–$C_6$) alkyl substituent; an aryl group; a halogen atom; a hydroxy group; a protected hydroxy group in which the protecting group is selected from substituents (b); a ($C_1$–$C_7$) alkanoyl group; a substituted ($C_2$–$C_7$) alkanoyl group having at least one of substituents (c); an arylcarbonyl group; a cycloalkylcarbonyl group in which the cycloalkyl part is ($C_3$–$C_{10}$); a substituted cycloalkylcarbonyl group in which the cycloalkyl part is ($C_3$–$C_{10}$) and has at least one ($C_1$–$C_6$) alkyl substituent; a carboxy group; a ($C_2$–$C_7$) alkoxycarbonyl group; an aryloxycarbonyl group; and aralkyloxycarbonyl group; a nitro group; a group of formula VIIb

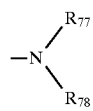

in which
R$_{77}$ and R$_{78}$ are the same or different and each represents a hydrogen atom, a (C$_1$–C$_6$) alkyl group, an aralkyl group, a (C$_3$–C$_{10}$) cycloalkyl group, an aryl group, a (C$_1$–C$_7$) alkanoyl group, an aralkanoyl group, an arylcarbonyl group or a (C$_2$–C$_7$) alkoxycarbonyl group, or R$_{77}$ and R$_{78}$, together with the nitrogen atom to which they are attached, form a nitrogen-containing heterocyclic group having from 5 to 10 ring atoms, of which one is said nitrogen atom and from 0 to 3 are additional nitrogen and/or oxygen and/or sulphur hetero-atoms;

or a group of formula VIIc

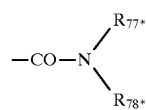

in which
R$_{77*}$ and R$_{78*}$ are the same or different and each represents a hydrogen atom, a (C$_1$–C$_6$) alkyl group, an aralkyl group, a (C$_3$–C$_{10}$) cycloalkyl group or an aryl group or R$_{77}$ and R$_{78}$, together with the nitrogen atom to which they are attached, form a nitrogen-containing heterocyclic group having from 5 to 10 ring atoms, of which one is said nitrogen atom and from 0 to 3 are independently additional nitrogen or oxygen or sulphur hetero-atoms;

R$_{73}$ represents a hydrogen atom, a (C$_1$–C$_{25}$) alkyl group, a substituted (C$_1$–C$_{25}$) alkyl group having at least one of substituents (a), an aralkyl group, a (C$_3$–C$_{10}$) cycloalkyl group, a substituted (C$_3$–C$_{10}$) cycloalkyl group having at least one (C$_1$–C$_6$) alkyl substituent, an aryl group, a halogen atom, a (C$_1$–C$_7$) alkanoyl group, a substituted (C$_2$–C$_7$) alkanoyl group having at least one of substituents (c), an arylcarbonyl group, a cycloalkylcarbonyl group in which the cycloalkyl part is (C$_3$–C$_{10}$) a substituted cycloalkylcarbonyl group in which the cycloalkyl part is (C$_3$–C$_{10}$) and has at least one (C$_1$–C$_6$) alkyl substituent, a carboxy group, a (C$_2$–C$_7$) alkoxycarbonyl group, an aryloxycarbonyl group, an aralkyloxycarbonyl group, a nitro group, a group of formula VIIb, as defined above, or a group of formula VIIc, as defined above; or R$_{73}$ represents a hydroxy group or a protected hydroxy group in which the protecting group is selected from substituents (b), provided that at least one of R$_{72}$, R$_{74}$ and R$_{75}$ represents a substituted alkyl group having at least one of substituents (a), a halogen atom, a hydroxy group, a substituted alkoxy group having at least one of substituents (c), a (C$_1$–C$_7$) alkanoyloxy group, a substituted (C$_2$–C$_7$) alkanoyloxy group having at least one of substituents (c), an arylcarbonyloxy group, a sulphoxy group, a (C$_1$–C$_7$) alkanoyl group, a substituted (C$_2$–C$_7$) alkanoyl group having at least one of substituents (c), a cycloalkylcarbonyl group in which the cycloalkyl part is, a substituted cycloalkylcarbonyl group in which the cycloalkyl part is (C$_3$–C$_{10}$) and has at least one (C$_1$–C$_8$) alkyl substituent, an arylcarbonyl group, a carboxy group, a (C$_2$–C$_7$) alkoxycarbonyl group, an aryloxycarbonyl group, an aralkyloxycarbonyl group, a nitro group, a group of formula VIIb, as defined above, or a group of formula VIIc, as defined above, Ar represents a divalent aromatic carbocyclic group or a divalent aromatic heterocyclic group; W represents a methylene group, a carbonyl group, a group of formula >CH—OY in which Y represents a hydrogen atom, a (C$_1$–C$_7$) alkanoyl group or an arylcarbonyl group, or a group of formula >C=N—OV in which V represents a hydrogen atom, a (C$_1$–C$_7$) alkyl group, a substituted (C$_1$–C$_6$) alkyl group having at least one of substituents (c), a (C$_1$–C$_7$) alkanoyl group or an arylcarbonyl group; U represents a single bond or a methylene group; or, when W represents a carbonyl group or said group of formula >C=N—OV, U, R$_{71}$ and the carbon atom to which R$_{71}$ is attached may together represent a group of formula —CH=C<; or when W represents a carbonyl group or said group of formula >C=N—OV, U, R$_{71}$ and the carbon atom to which R$_{71}$ is attached may together represent a group of formula —CH=C<; or W-U may represent a carbon-carbon double bond; and n represents an integer from 1 to 10; said aralkyl groups have an alkyl portion containing from 1 to 6 carbon atoms and an aryl portion as defined below, the alkyl portion being unsubstituted or having at least one of substituents (c);

substituents (a):
hydroxy groups; protected hydroxy groups in which the protecting group is selected from substituents (b); (C$_1$–C$_7$) aliphatic carboxylic acyl groups; (C$_2$–C$_7$) aliphatic carboxylic acyl groups having at least one of substituents (c); arylcarbonyl groups; cycloalkylcarbonyl groups in which the cycloalkyl part is (C$_3$–C$_{10}$); substituted cycloalkylcarbonyl groups in which the cycloalkyl part is (C$_3$–C$_{10}$) and having at least one (C$_1$–C$_6$) alkyl substituent; carboxy groups; (C$_2$–C$_7$) alkoxycarbonyl groups; aryloxycarbonyl groups; aralkyloxy-carbonyl groups; hydroxyimino groups; protected hydroxyimino groups in which the protecting group is selected from substituents (b); groups of formula VIIb, as defined above; and groups of formula VIIc, as defined above;

substituents (b):
(C$_1$–C$_6$) alkyl groups, substituted (C$_1$–C$_6$) alkyl groups having at least one of substituents (c), (C$_1$–C$_7$) aliphatic carboxylic acyl groups, substituted (C$_2$–C$_7$) aliphatic carboxylic acyl groups having at least one of substituents (c), arylcarbonyl groups, (C$_2$–C$_7$) alkoxycarbonyl groups, aryloxycarbonyl groups, groups of formula (VIIc), as defined above and sulpho groups;

substituents (c):
carboxy groups, (C$_2$–C$_7$). alkoxycarbonyl groups and aryl groups;

said aryl groups and the aryl parts of said aralkyl, arylcarbonyl, aryloxycarbonyl, aralkyloxycarbonyl and divalent aromatic groups being (C$_6$–C$_{14}$) carbocyclic aryl groups which are unsubstituted or have at least one of substituents (d);

said heterocyclic groups, heterocyclic parts of said heterocyclic acyl and acyloxy groups and said divalent heterocyclic aromatic groups have from 5 to 14 ring atoms, of which from 1 to 5 are independently nitrogen, oxygen or sulphur hetero-atoms, said heterocyclic groups being unsubstituted or having at least one substituent selected from substituents (d) and substituents (e);

substituents (d):
- ($C_1$–$C_6$) alkyl groups, ($C_1$–$C_6$) alkoxy groups, hydroxy groups, sulphoxy groups, halogen atoms, nitro groups, groups of formula (II), as defined above, ($C_1$–$C_7$) aliphatic carboxylic acyl groups, ($C_7$–$C_{11}$) arylcarbonyloxy groups in which the aryl part is unsubstituted or has at least one substituent selected from ($C_1$–$C_6$) alkyl groups, ($C_1$–$C_6$) alkoxy groups and halogen atoms;

substituents (e):
- aryl groups and oxygen atoms.

10. A method of claim 1 wherein the thiazolidine derivative is further selected from compounds where X is methylene and $R_1$ is of formula VIII

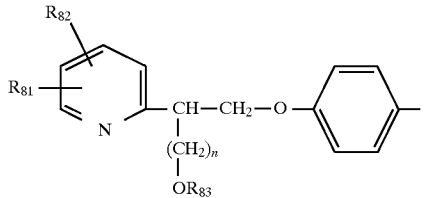

wherein $R_{81}$ and $R_{82}$ are the same or different and each represent hydrogen or a lower alkyl group; $R_{83}$ is hydrogen or acyl group; n is 0 or 1.

11. A method of claim 2 wherein the thiazolidine-dione is selected from compounds where X is a bond and $R_1$ is of formula IX

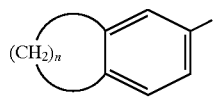

where n is an integer of 3 to 6.

12. A method of claim 2 wherein the thiazolidinedione is selected from compounds where $R_1$ is of the formula XI

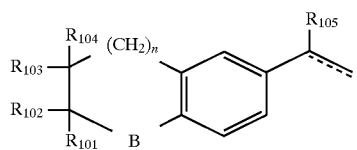

wherein the broken line is a bond or no bond, n is zero, 1 or 2; B is O,S, >S=O, >S(=O)$_2$; $R_{105}$ is H, $CH_3$, or $C_2H_5$; when taken separately, $R_{101}$ is H, ($C_5$–$C_7$) cycloalkyl, ($C_6$–$C_8$) methyl-substituted cycloalkyl, pyridyl, thienyl, furyl, naphthyl, p-biphenylyl, tetrahydrofuranyl, tetrahydrothienyl, tetrahydropyranyl, $C_6H_4W_2$ or alk-$W_1$ and alk is ($C_1$–$C_6$) alkylene, ethylidene or isopropylidene; $W_1$ is H, OH, ($C_1$–$C_4$) alkoxy, ($C_1$–$C_4$) thioalkyl, pyridyl, furyl, thienyl, tetrahydrofuryl, tetrahydrothienyl, naphthyl, ($C_5$–$C_7$) cycyloalkyl or $C_6H_4W_2$ and $W_2$ is H, OH, F, Cl, Br, ($C_1$–$C_4$) alkyl, ($C_1$–$C_4$) alkoxy or ($C_1$–$C_4$) thioalkyl; $R_{102}$ is H or $CH_3$, $R_{103}$ is H, ($C_1$–$C_6$) alkyl, $C_6H_4W_2$ or benzyl; and $R_{104}$ is H; when $R_{101}$ and $R_{102}$ are taken together they form ($C_4$–$C_6$) alkylene and $R_{103}$ and $R_{104}$ are each H; when $R_{103}$ and $R_{104}$ are taken together they form ($C_4$–$C_6$) alkylene and $R_{101}$ and $R_{102}$ are each H; and when $R_{102}$ and $R_{103}$ are taken together they are ($C_3$–$C_4$) alkylene and $R_{101}$ and $R_{104}$ are each H.

13. A method of claim 12 wherein $R_{105}$ is H.

14. A method of claim 13 wherein X is a single bond.

15. A method of claim 14 wherein n is zero or 1.

16. A method of claim 15 wherein $R_{102}$, $R_{103}$ and $R_{104}$ are each H and $R_{101}$ is H, cyclohexyl, $C_6H_4W_2$ or alk-$W_1$ where alk is ($C_1$–$C_4$) alkylene, ethylidene, or isopropylidene; $W_1$ is HR, OH, ($C_1$–$C_4$) alkoxy, cyclohexyl or $C_6H_4W_2$ and $W_2$ is H, F, Cl, Br, $CH_3$, or $CH_3O$.

17. A method of claim 16 wherein B is oxo, n is 1 and $R_{101}$ is benzyl.

18. A method of claim 1 wherein the administration is topical.

19. A method of claim 1 wherein the administration is oral.

20. A method of claim 19 wherein the effective amount is selected from the range of from about 200 mg to about 400 mg.

21. A method for treating acne vulgaris in a human in need thereof by administration of an effective amount of a 5-aryl substituted thiazolidine derivative of formula I

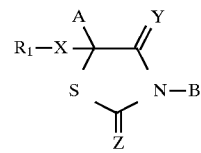

where:
A is H or methyl;
B is H or methyl;
X is a lower alkylene or a bond or —HC=CH—;
Y is oxo or imino;
Z is oxo or imino;
$R_1$ is a substituted unsaturated carbocyclic compound of formula IIa

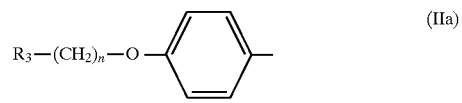

wherein n is an integer of 1–4 and $R_3$ is a compound of formula IIf

wherein A' is an aromatic heterocyclic group and A" is an alkyl group;
and pharmaceutically acceptable salts thereof.

* * * * *

UNITED STATES PATENT AND TRADEMARK OFFICE
CERTIFICATE OF CORRECTION

PATENT NO. : 5,824,694
DATED : October 20, 1998
INVENTOR(S) : Theodore W. Kurtz and Harrihar A. Pershadsingh It is certified that error appears in the above-indentified patent and that said Letters Patent is hereby corrected as shown below:

In the title, in item [54] of the cover sheet and in column 1,

Change the title to --THIAZOLIDINE DERIVATIVES FOR THE TREATMENT OF ACNE--.

At col. 5, in formula IV, at lines 6-10, and in formula V, at lines 25-30, add a phenyl to the oxygen as set forth below:

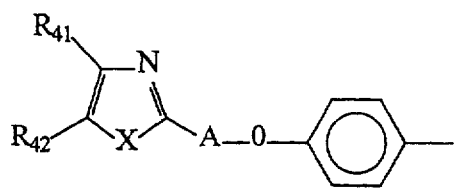 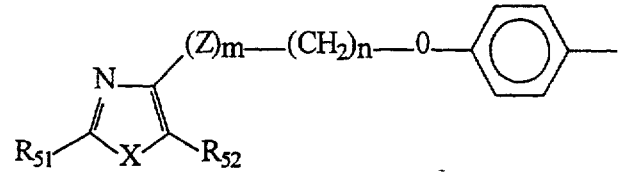

UNITED STATES PATENT AND TRADEMARK OFFICE
CERTIFICATE OF CORRECTION

PATENT NO. : 5,824,694
DATED : October 20, 1998
INVENTOR(S) : Theodore W. Kurtz and Harrihar A. Pershadsingh It is certified that error appears in the above-indentified patent and that said Letters Patent is hereby corrected as shown below:

In col. 5, in formula VI, at lines 50-56, add a phenyl to the oxygen as set forth below:

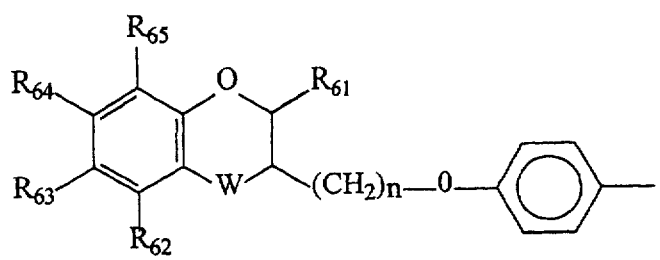

UNITED STATES PATENT AND TRADEMARK OFFICE
CERTIFICATE OF CORRECTION

PATENT NO. : 5,824,694
DATED : October 20, 1998
INVENTOR(S) : Theodore W. Kurtz and Harrihar A. Pershadsingh

*It is certified that error appears in the above-indentified patent and that said Letters Patent is hereby corrected as shown below:*

In col. 6, line 24, add a variable "U" for the carbon at position 3.

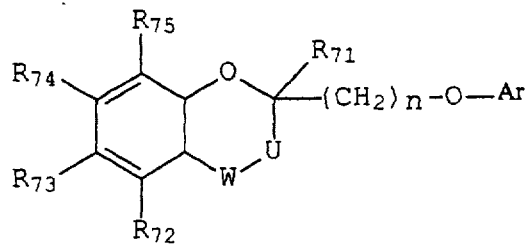

In col. 16, in formula IV, at lines 58-64, add a phenyl to the oxygen.

In col. 18, in formula V, at lines 22-27, add a phenyl to the oxygen.

In col. 19, in formula VI, at lines 5-12, add a phenyl to the oxygen.

UNITED STATES PATENT AND TRADEMARK OFFICE
CERTIFICATE OF CORRECTION

PATENT NO. : 5,824,694
DATED : October 20, 1998
INVENTOR(S) : Theodore W. Kurtz and Harrihar A. Pershadsingh It is certified that error appears in the above-indentified patent and that said Letters Patent is hereby corrected as shown below:

In claim 1, line 17, delete both occurrences of "unsaturated" and insert therefor --aromatic--.

In claim 6, col. 37, at line 38, add a phenol to the oxygen, i.e.,

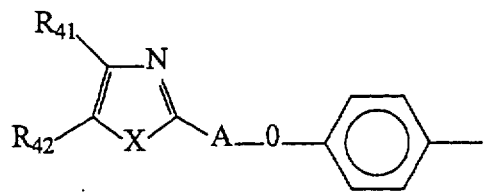

UNITED STATES PATENT AND TRADEMARK OFFICE
CERTIFICATE OF CORRECTION

PATENT NO. : 5,824,694                                    Page 5 of 6
DATED     : October 20, 1998
INVENTOR(S) : Theodore W. Kurtz and Harrihar A. Pershadsingh It is certified that error appears in the above-indentified patent and that said Letters Patent is hereby corrected as shown below:

In claim 7, col. 37, at line 49, add a phenol to the oxygen, i.e.,

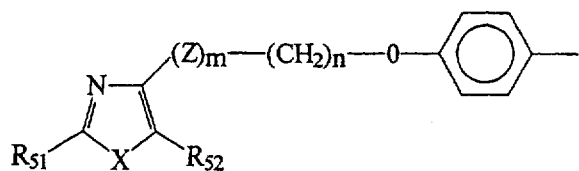

In claim 8, col. 38, line 7, add a phenol to the oxygen, i.e.,

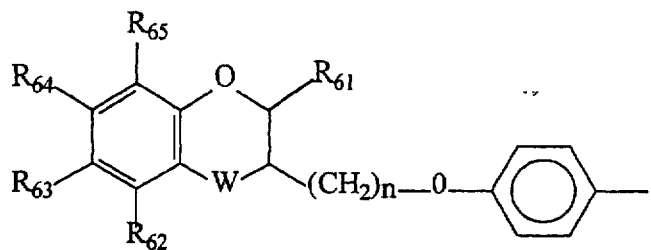

UNITED STATES PATENT AND TRADEMARK OFFICE
CERTIFICATE OF CORRECTION

PATENT NO. : 5,824,694
DATED : October 20, 1998
INVENTOR(S) : Theodore W. Kurtz and Harringar A. Pershadsingh It is certified that error appears in the above-indentified patent and that said Letters Patent is hereby corrected as shown below:

In claim 9, col.38, line 49, cahnge formula VII to add --U-- as follows:

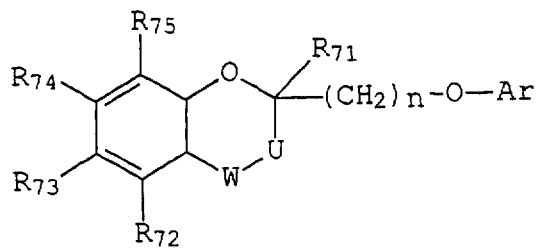

Signed and Sealed this

Twentieth Day of March, 2001

Attest:

NICHOLAS P. GODICI

Attesting Officer    Acting Director of the United States Patent and Trademark Office